US011767537B2

(12) United States Patent
Young et al.

(10) Patent No.: US 11,767,537 B2
(45) Date of Patent: Sep. 26, 2023

(54) MAMMALIAN EXPRESSION SYSTEM

(71) Applicant: LONZA BIOLOGICS PLC., Slough (GB)

(72) Inventors: Robert Young, London (GB); James D. Budge, Canterbury (GB); Mark C. Smales, Canterbury (GB)

(73) Assignee: LONZA BIOLOGICS PLC., Slough (GB)

( * ) Notice: Subject to any disclaimer, the term of this patent is extended or adjusted under 35 U.S.C. 154(b) by 964 days.

(21) Appl. No.: 15/754,881

(22) PCT Filed: Aug. 25, 2016

(86) PCT No.: PCT/EP2016/070083
§ 371 (c)(1),
(2) Date: Feb. 23, 2018

(87) PCT Pub. No.: WO2017/032834
PCT Pub. Date: Mar. 2, 2017

(65) Prior Publication Data
US 2020/0291423 A1 Sep. 17, 2020

(30) Foreign Application Priority Data

Aug. 25, 2015 (EP) .................................. 15182412

(51) Int. Cl.
| | |
|---|---|
| *C12N 15/85* | (2006.01) |
| *C07K 14/005* | (2006.01) |
| *C07K 16/00* | (2006.01) |
| *C12N 5/071* | (2010.01) |
| *C12N 7/00* | (2006.01) |
| *C12N 9/12* | (2006.01) |
| *C12N 15/67* | (2006.01) |

(52) U.S. Cl.
CPC ............ *C12N 15/85* (2013.01); *C07K 14/005* (2013.01); *C07K 16/00* (2013.01); *C12N 5/0682* (2013.01); *C12N 7/00* (2013.01); *C12N 9/1229* (2013.01); *C12N 15/67* (2013.01); *C12Y 207/04004* (2013.01); *C12N 2800/108* (2013.01)

(58) Field of Classification Search
None
See application file for complete search history.

(56) References Cited

FOREIGN PATENT DOCUMENTS

| | | | | |
|---|---|---|---|---|
| WO | WO-2006096989 A2 * | 9/2006 | ........... | C07K 14/005 |
| WO | 2007048601 A1 | 5/2007 | | |

OTHER PUBLICATIONS

Kaul et al Journal of Virology, 81, 10352-10361 (Year: 2007).*
Daramola et al Biotechnol. Prog., 30:132-141 (Year: 2014).*
Munkonge et al Journal of Biological Chemistry, 284, (39), 369078-26987 (Year: 2009).*
Durocher et al Nucleic acid Research 30, 2 e9, 1-9 (pp. 1-28) (Year: 2002).*
Kirchmaier et al Journal of Virology, 1280-1283 (Year: 1995).*
Accession No. JI885523, p. 1-2 (Year: 2011).*
Murakami et al (Journal of Virology 1559-1568 (Year: 2005).*
Magistrelli et al Protein Purification, ed R Ahmad, p. 73-88 (Year: 2012).*
Fan et al Biotechnology and Bioengineering, vol. 109, No. 4, (Year: 2012).*
Costa et al European Journal of Pharmaceutics and Biopharmaceutics 74, 127-138 (Year: 2010).*
International Search Report and Written Opinion in corresponding International Application No. PCT/EP2016/070083, dated Nov. 21, 2016 (12 pages).
Saha et al., FEES Letters, 585: 3174-3184 (2011).
Kaul et al., Journal of Virology, 81: 10352-10361 (2007).
Murakami et al., Journal of Virology, 79: 1559-1568 (2005).
Budge, James D; et al. "Engineering of Chinese Hamster Ovary Cells With NDPK-A to Enhance DNA Nuclear Delivery Combined With EBNA1 Plasmid Maintenance Gives Improved Exogenous Transient Reporter, mAb and SARS-CoV-2 Spike Protein Expression." Frontiers in bioengineering and biotechnology vol. 9 679448. Jun. 4, 2021, doi:10.3389/fbioe.2021.679448.

* cited by examiner

*Primary Examiner* — Anoop K Singh
(74) *Attorney, Agent, or Firm* — Lucas & Mercanti, LLP

(57) ABSTRACT

The present invention relates to an expression system for the heterologous expression of a nucleic acid sequence of interest in a mammalian cell, the system comprising: (i) a first genetic entity, comprising: a nucleic acid sequence encoding a functional Epstein Barr virus nuclear antigen 1 (EBNA-1), the nucleic acid sequence being operably linked to regulatory elements that allow for expression of the nucleic acid sequence encoding a functional EBNA-1; (ii) a second genetic entity, comprising: a nucleic acid sequence encoding a functional nucleoside diphosphate kinase A (NDPK-A), the nucleic acid sequence being operably linked to regulatory elements that allow for expression of the nucleic acid sequence encoding a functional NDPK-A; (iii) a third genetic entity, comprising: the nucleic acid sequence of interest being operably linked to regulatory elements that allow for expression of the nucleic acid sequence of interest; and (iv) a four genetic entity, comprising: the Epstein Barr virus OriP sequence or one or more subsequences thereof, wherein the one or more subsequences comprise at least the 'Family of Repeats' DNA-binding site for EBNA-1 and the 'Dyad Symmetry' DNA-binding site for EBNA-1. The present invention also relates to corresponding mammalian host cells and methods for expressing a nucleic acid sequence of interest by means of such expression system.

12 Claims, 15 Drawing Sheets

Specification includes a Sequence Listing.

A

B

C

D

A

B

C

D

A

B

C

D

A

| Vectors |  eGFP |  NDPK-A eGFP |  EBNA-1 eGFP oriP regions |
|---|---|---|---|
| Control/Control | ✓✓ | ✗ | ✗ |
| NDPK-A/Control | ✓ | ✓ | ✗ |
| EBNA-1/Control | ✓ | ✗ | ✓ |
| EBNA-1/NDPK-A | ✗ | ✓ | ✓ |

B

C

D

E

A

B

C

D

SEQUENCE LISTING

```
<160> NUMBER OF SEQ ID NOS: 15

<210> SEQ ID NO 1
<211> LENGTH: 1926
<212> TYPE: DNA
<213> ORGANISM: Human herpesvirus 4 (Epstein-Barr virus)
<220> FEATURE:
<221> NAME/KEY: CDS
<222> LOCATION: (1)..(1926)

<400> SEQUENCE: 1 atg tct gac gag ggg cca ggt aca gga cct gga aat ggc cta gga gag      48
Met Ser Asp Glu Gly Pro Gly Thr Gly Pro Gly Asn Gly Leu Gly Glu
1               5                   10                  15 aag gga gac aca tct gga cca gaa ggc tcc ggc ggc agt gga cct caa      96
Lys Gly Asp Thr Ser Gly Pro Glu Gly Ser Gly Gly Ser Gly Pro Gln
            20                  25                  30 aga aga ggg ggt gat aac cat gga cga gga cgg gga aga gga cga gga     144
Arg Arg Gly Gly Asp Asn His Gly Arg Gly Arg Gly Arg Gly Arg Gly
        35                  40                  45 cga gga ggc gga aga cca gga gcc ccg ggc ggc tca gga tca ggg cca     192
Arg Gly Gly Gly Arg Pro Gly Ala Pro Gly Gly Ser Gly Ser Gly Pro
    50                  55                  60 aga cat aga gat ggt gtc cgg aga ccc caa aaa cgt cca agt tgc att     240
Arg His Arg Asp Gly Val Arg Arg Pro Gln Lys Arg Pro Ser Cys Ile
65                  70                  75                  80 ggc tgc aaa ggg acc cac ggt gga aca gga gca gga gca gga gcg gga     288
Gly Cys Lys Gly Thr His Gly Gly Thr Gly Ala Gly Ala Gly Ala Gly
                85                  90                  95 ggg gca gga gca gga ggg gca gga gca gga ggg gca gga gca gga        336
Gly Ala Gly Ala Gly Gly Ala Gly Ala Gly Gly Gly Ala Gly Ala Gly
```

-continued

|  |  |  |  |
|---|---|---|---|
| gga ggg gca gga ggg gca gga ggg gca gga ggg gca gga gca gga gga<br>Gly Gly Ala Gly Gly Ala Gly Gly Ala Gly Gly Ala Gly Ala Gly Gly<br>115                    120                    125 | 384 |
| ggg gca gga gca gga gga ggg gca gga ggg gca gga ggg gca gga gca<br>Gly Ala Gly Ala Gly Gly Gly Ala Gly Gly Ala Gly Gly Ala Gly Ala<br>     130                    135                    140 | 432 |
| gga gga ggg gca gga gca gga gga ggg gca gga ggg gca gga gca gga<br>Gly Gly Gly Ala Gly Ala Gly Gly Gly Ala Gly Gly Ala Gly Ala Gly<br>145                    150                    155                    160 | 480 |
| gga ggg gca gga ggg gca gga ggg gca gga gca gga ggg gca gga<br>Gly Gly Ala Gly Gly Ala Gly Gly Ala Gly Ala Gly Gly Ala Gly<br>                165                    170                    175 | 528 |
| gaa gga gga ggg gca gga ggg gca gga gca gga gga ggg gca gga ggg<br>Glu Gly Gly Gly Ala Gly Gly Ala Gly Ala Gly Gly Gly Ala Gly Gly<br>     180                    185                    190 | 576 |
| gca gga ggg gca gga gca gga gga ggg gca gga gca gga ggg gca gga<br>Ala Gly Gly Ala Gly Ala Gly Gly Gly Ala Gly Ala Gly Gly Ala Gly<br>195                    200                    205 | 624 |
| ggg gca gga ggg gca gga gca gga ggg gca gga gca gga gga ggg gca<br>Gly Ala Gly Gly Ala Gly Ala Gly Gly Ala Gly Ala Gly Gly Gly Ala<br>     210                    215                    220 | 672 |
| gga ggg gca gga ggg gca gga gca gga ggg gca gga gca gga ggg gca<br>Gly Gly Ala Gly Gly Ala Gly Ala Gly Gly Ala Gly Ala Gly Gly Ala<br>225                    230                    235                    240 | 720 |
| gga gca gga ggg gca gga gca gga ggg gca gga ggg gca gga gca gga<br>Gly Ala Gly Gly Ala Gly Ala Gly Gly Ala Gly Gly Ala Gly Ala Gly<br>                245                    250                    255 | 768 |
| ggg gca gga ggg gca gga gca gga ggg gca gga ggg gca gga gca gga<br>Gly Ala Gly Gly Ala Gly Ala Gly Gly Ala Gly Gly Ala Gly Ala Gly<br>     260                    265                    270 | 816 |
| gga ggg gca gga ggg gca gga gca gga gga ggg gca gga ggg gca gga<br>Gly Gly Ala Gly Gly Ala Gly Ala Gly Gly Gly Ala Gly Gly Ala Gly<br>                275                    280                    285 | 864 |
| gca gga ggg gca gga ggg gca gga gca gga ggg gca gga ggg gca gga<br>Ala Gly Gly Ala Gly Gly Ala Gly Ala Gly Gly Ala Gly Gly Ala Gly<br>     290                    295                    300 | 912 |
| gca gga ggg gca gga ggg gca gga gca gga gga ggg gca gga gca gga<br>Ala Gly Gly Ala Gly Gly Ala Gly Ala Gly Gly Gly Ala Gly Ala Gly<br>305                    310                    315                    320 | 960 |
| ggg gca gga gca gga ggt gga ggc cgg ggt cga gga ggc agt gga ggc<br>Gly Ala Gly Ala Gly Gly Gly Gly Arg Gly Arg Gly Gly Ser Gly Gly<br>                325                    330                    335 | 1008 |
| cgg ggt cga gga ggt agt gga ggc cgg ggt cga gga ggt agt gga ggc<br>Arg Gly Arg Gly Gly Ser Gly Gly Arg Gly Arg Gly Gly Ser Gly Gly<br>                340                    345                    350 | 1056 |
| cgc cgg ggt aga gga cgt gaa aga gcc agg ggg gga agt cgt gaa aga<br>Arg Arg Gly Arg Gly Arg Glu Arg Ala Arg Gly Gly Ser Arg Glu Arg<br>              355                    360                    365 | 1104 |
| gcc agg ggg aga ggt cgt gga cgt gga gaa aag agg ccc agg agt ccc<br>Ala Arg Gly Arg Gly Arg Gly Arg Gly Glu Lys Arg Pro Arg Ser Pro<br>     370                    375                    380 | 1152 |
| agt agt cag tca tca tca tcc ggg tct cca ccg cgc agg ccc cct cca<br>Ser Ser Gln Ser Ser Ser Ser Gly Ser Pro Pro Arg Arg Pro Pro Pro<br>385                    390                    395                    400 | 1200 |
| ggt aga agg cca ttt ttc cac cct gta ggg gaa gcc gat tat ttt gaa<br>Gly Arg Arg Pro Phe Phe His Pro Val Gly Glu Ala Asp Tyr Phe Glu<br>                405                    410                    415 | 1248 |
| tac cac caa gaa ggt ggc cca gat ggt gag cct gac gtg ccc ccg gga | 1296 |

```
Tyr His Gln Glu Gly Gly Pro Asp Gly Glu Pro Asp Val Pro Pro Gly
                    420                 425                 430 gcg ata gag cag ggc ccc gca gat gac cca gga gaa ggc cca agc act    1344
Ala Ile Glu Gln Gly Pro Ala Asp Asp Pro Gly Glu Gly Pro Ser Thr
            435                 440                 445 gga ccc cgg ggt cag ggt gat gga ggc agg cgc aaa aaa gga ggg tgg    1392
Gly Pro Arg Gly Gln Gly Asp Gly Gly Arg Arg Lys Lys Gly Gly Trp
        450                 455                 460 ttt gga aag cat cgt ggt caa gga ggt tcc aac ccg aaa ttt gag aac    1440
Phe Gly Lys His Arg Gly Gln Gly Gly Ser Asn Pro Lys Phe Glu Asn
465                 470                 475                 480 att gca gaa ggt tta aga gct ctc ctg gct agg agt cac gta gaa agg    1488
Ile Ala Glu Gly Leu Arg Ala Leu Leu Ala Arg Ser His Val Glu Arg
                    485                 490                 495 act acc gac gaa gga act tgg gtc gcc ggt gtg ttc gta tat gga ggt    1536
Thr Thr Asp Glu Gly Thr Trp Val Ala Gly Val Phe Val Tyr Gly Gly
                500                 505                 510 agt aag acc tcc ctt tac aac cta agg cga gga act gcc ctt gct att    1584
Ser Lys Thr Ser Leu Tyr Asn Leu Arg Arg Gly Thr Ala Leu Ala Ile
            515                 520                 525 cca caa tgt cgt ctt aca cca ttg agt cgt ctc ccc ttt gga atg gcc    1632
Pro Gln Cys Arg Leu Thr Pro Leu Ser Arg Leu Pro Phe Gly Met Ala
        530                 535                 540 cct gga ccc ggc cca caa cct ggc ccg cta agg gag tcc att gtc tgt    1680
Pro Gly Pro Gly Pro Gln Pro Gly Pro Leu Arg Glu Ser Ile Val Cys
545                 550                 555                 560 tat ttc atg gtc ttt tta caa act cat ata ttt gct gag gtt ttg aag    1728
Tyr Phe Met Val Phe Leu Gln Thr His Ile Phe Ala Glu Val Leu Lys
                    565                 570                 575 gat gcg att aag gac ctt gtt atg aca aag ccc gct cct acc tgc aat    1776
Asp Ala Ile Lys Asp Leu Val Met Thr Lys Pro Ala Pro Thr Cys Asn
                580                 585                 590 atc agg gtg act gtg tgc agc ttt gac gat gga gta gat ttg cct ccc    1824
Ile Arg Val Thr Val Cys Ser Phe Asp Asp Gly Val Asp Leu Pro Pro
            595                 600                 605 tgg ttt cca cct atg gtg gaa ggg gct gcc gcg gag ggt gat gac gga    1872
Trp Phe Pro Pro Met Val Glu Gly Ala Ala Ala Glu Gly Asp Asp Gly
        610                 615                 620 gat gac gga gat gaa gga ggt gat gga gat gag ggt gag gaa ggg cag    1920
Asp Asp Gly Asp Glu Gly Gly Asp Gly Asp Glu Gly Glu Glu Gly Gln
625                 630                 635                 640 gag tga                                                            1926
Glu

<210> SEQ ID NO 2
<211> LENGTH: 1254
<212> TYPE: DNA
<213> ORGANISM: Artificial Sequence
<220> FEATURE:
<223> OTHER INFORMATION: truncated Epstein-Barr virus nuclear antigen 1
      cDNA
<220> FEATURE:
<221> NAME/KEY: CDS
<222> LOCATION: (1)..(1254)

<400> SEQUENCE: 2 atg tct gac gag ggg cca ggt aca gga cct gga aat ggc cta gga gag    48
Met Ser Asp Glu Gly Pro Gly Thr Gly Pro Gly Asn Gly Leu Gly Glu
1               5                   10                  15 aag gga gac aca tct gga cca gaa ggc tcc ggc ggc agt gga cct caa    96
Lys Gly Asp Thr Ser Gly Pro Glu Gly Ser Gly Gly Ser Gly Pro Gln
            20                  25                  30
```

-continued

```
aga aga ggg ggt gat aac cat gga cga gga cgg gga aga gga cga gga      144
Arg Arg Gly Gly Asp Asn His Gly Arg Gly Arg Gly Arg Gly Arg Gly
         35                  40                  45 cga gga ggc gga aga cca gga gcc ccg ggc ggc tca gga tca ggg cca      192
Arg Gly Gly Gly Arg Pro Gly Ala Pro Gly Gly Ser Gly Ser Gly Pro
 50                  55                  60 aga cat aga gat ggt gtc cgg aga ccc caa aaa cgt cca agt tgc att      240
Arg His Arg Asp Gly Val Arg Arg Pro Gln Lys Arg Pro Ser Cys Ile
 65                  70                  75                  80 ggc tgc aaa ggg acc cac ggt gga aca gga gca gga gca gga gcg gga      288
Gly Cys Lys Gly Thr His Gly Gly Thr Gly Ala Gly Ala Gly Ala Gly
                 85                  90                  95 ggg gca gga gca gga ggt gga ggc cgg ggt cga gga ggc agt gga ggc      336
Gly Ala Gly Ala Gly Gly Gly Gly Arg Gly Arg Gly Gly Ser Gly Gly
            100                 105                 110 cgg ggt cga gga ggt agt gga ggc cgg ggt cga gga ggt agt gga ggc      384
Arg Gly Arg Gly Gly Ser Gly Gly Arg Gly Arg Gly Gly Ser Gly Gly
            115                 120                 125 cgc cgg ggt aga gga cgt gaa aga gcc agg ggg gga agt cgt gaa aga      432
Arg Arg Gly Arg Gly Arg Glu Arg Ala Arg Gly Gly Ser Arg Glu Arg
130                 135                 140 gcc agg ggg aga ggt cgt gga cgt gga gaa aag agg ccc agg agt ccc      480
Ala Arg Gly Arg Gly Arg Gly Arg Gly Glu Lys Arg Pro Arg Ser Pro
145                 150                 155                 160 agt agt cag tca tca tca tcc ggg tct cca ccg cgc agg ccc cct cca      528
Ser Ser Gln Ser Ser Ser Ser Gly Ser Pro Pro Arg Arg Pro Pro Pro
                165                 170                 175 ggt aga agg cca ttt ttc cac cct gta ggg gaa gcc gat tat ttt gaa      576
Gly Arg Arg Pro Phe Phe His Pro Val Gly Glu Ala Asp Tyr Phe Glu
            180                 185                 190 tac cac caa gaa ggt ggc cca gat ggt gag cct gac gtg ccc ccg gga      624
Tyr His Gln Glu Gly Gly Pro Asp Gly Glu Pro Asp Val Pro Pro Gly
            195                 200                 205 gcg ata gag cag ggc ccc gca gat gac cca gga gaa ggc cca agc act      672
Ala Ile Glu Gln Gly Pro Ala Asp Asp Pro Gly Glu Gly Pro Ser Thr
210                 215                 220 gga ccc cgg ggt cag ggt gat gga ggc agg cgc aaa aaa gga ggg tgg      720
Gly Pro Arg Gly Gln Gly Asp Gly Gly Arg Arg Lys Lys Gly Gly Trp
225                 230                 235                 240 ttt gga aag cat cgt ggt caa gga ggt tcc aac ccg aaa ttt gag aac      768
Phe Gly Lys His Arg Gly Gln Gly Gly Ser Asn Pro Lys Phe Glu Asn
                245                 250                 255 att gca gaa ggt tta aga gct ctc ctg gct agg agt cac gta gaa agg      816
Ile Ala Glu Gly Leu Arg Ala Leu Leu Ala Arg Ser His Val Glu Arg
            260                 265                 270 act acc gac gaa gga act tgg gtc gcc ggt gtg ttc gta tat gga ggt      864
Thr Thr Asp Glu Gly Thr Trp Val Ala Gly Val Phe Val Tyr Gly Gly
            275                 280                 285 agt aag acc tcc ctt tac aac cta agg cga gga act gcc ctt gct att      912
Ser Lys Thr Ser Leu Tyr Asn Leu Arg Arg Gly Thr Ala Leu Ala Ile
            290                 295                 300 cca caa tgt cgt ctt aca cca ttg agt cgt ctc ccc ttt gga atg gcc      960
Pro Gln Cys Arg Leu Thr Pro Leu Ser Arg Leu Pro Phe Gly Met Ala
305                 310                 315                 320 cct gga ccc ggc cca caa cct ggc ccg cta agg gag tcc att gtc tgt     1008
Pro Gly Pro Gly Pro Gln Pro Gly Pro Leu Arg Glu Ser Ile Val Cys
                325                 330                 335 tat ttc atg gtc ttt tta caa act cat ata ttt gct gag gtt ttg aag     1056
Tyr Phe Met Val Phe Leu Gln Thr His Ile Phe Ala Glu Val Leu Lys
```

```
                    340                 345                 350
gat gcg att aag gac ctt gtt atg aca aag ccc gct cct acc tgc aat      1104
Asp Ala Ile Lys Asp Leu Val Met Thr Lys Pro Ala Pro Thr Cys Asn
            355                 360                 365 atc agg gtg act gtg tgc agc ttt gac gat gga gta gat ttg cct ccc      1152
Ile Arg Val Thr Val Cys Ser Phe Asp Asp Gly Val Asp Leu Pro Pro
    370                 375                 380 tgg ttt cca cct atg gtg gaa ggg gct gcc gcg gag ggt gat gac gga      1200
Trp Phe Pro Pro Met Val Glu Gly Ala Ala Ala Glu Gly Asp Asp Gly
385                 390                 395                 400 gat gac gga gat gaa gga ggt gat gga gat gag ggt gag gaa ggg cag      1248
Asp Asp Gly Asp Glu Gly Gly Asp Gly Asp Glu Gly Glu Glu Gly Gln
                405                 410                 415 gag tga                                                               1254
Glu

<210> SEQ ID NO 3
<211> LENGTH: 459
<212> TYPE: DNA
<213> ORGANISM: Cricetulus griseus (Chinese hamster)
<220> FEATURE:
<223> OTHER INFORMATION: nucleoside diphosphate kinase A cDNA
<220> FEATURE:
<221> NAME/KEY: CDS
<222> LOCATION: (1)..(459)

<400> SEQUENCE: 3 atg gcc aac agt gag cgc acc ttc att gct atc aag cct gat ggg gtc       48
Met Ala Asn Ser Glu Arg Thr Phe Ile Ala Ile Lys Pro Asp Gly Val
1               5                  10                  15 cag cgg ggt ctg gtg ggc gag atc atc aag cgt ttt gaa cag aag gga       96
Gln Arg Gly Leu Val Gly Glu Ile Ile Lys Arg Phe Glu Gln Lys Gly
            20                  25                  30 ttc cga ctt gtt ggc ctg aaa ttt atg cag gct tca gag gac ctt ctc      144
Phe Arg Leu Val Gly Leu Lys Phe Met Gln Ala Ser Glu Asp Leu Leu
        35                  40                  45 aaa gag cac tac att gac ctg aag gac cgt ccc ttc ttt act ggc cta      192
Lys Glu His Tyr Ile Asp Leu Lys Asp Arg Pro Phe Phe Thr Gly Leu
    50                  55                  60 gtg aaa tac atg cat tca gga cca gtg gtt gct atg gtc tgg gag ggg      240
Val Lys Tyr Met His Ser Gly Pro Val Val Ala Met Val Trp Glu Gly
65                  70                  75                  80 ttg aat gtt gtg aag aca ggc cgg gtg atg ctt gga gag acc aac cct      288
Leu Asn Val Val Lys Thr Gly Arg Val Met Leu Gly Glu Thr Asn Pro
                85                  90                  95 gca gac tct aaa cct ggg acc att cga gga gac ttt tgc atc caa gtt      336
Ala Asp Ser Lys Pro Gly Thr Ile Arg Gly Asp Phe Cys Ile Gln Val
            100                 105                 110 ggc agg aac atc att cat ggc agc gat tct gtg gag agt gca gag aag      384
Gly Arg Asn Ile Ile His Gly Ser Asp Ser Val Glu Ser Ala Glu Lys
        115                 120                 125 gag atc ggc ttg tgg ttt cag cct gag gag ctg gtg gat tac aag agc      432
Glu Ile Gly Leu Trp Phe Gln Pro Glu Glu Leu Val Asp Tyr Lys Ser
    130                 135                 140 tgt gca caa aac tgg atc tat gag tga                                  459
Cys Ala Gln Asn Trp Ile Tyr Glu
145                 150

<210> SEQ ID NO 4
<211> LENGTH: 494
<212> TYPE: DNA
<213> ORGANISM: Human herpesvirus 4 (Epstein-Barr virus)
```

-continued

```
<220> FEATURE:
<223> OTHER INFORMATION: Origin of replication P (OriP) 'Family of
      Repeats' region

<400> SEQUENCE: 4
ggatagcata tgctacccag atatagatta ggatagccta tgctacccag atataaatta      60
ggatagcata tactacccag atatagatta ggatagcata tgctacccag atatagatta     120
ggatagccta tgctacccag atatagatta ggatagcata tgctacccag atatagatta     180
ggatagcata tgcaatccag atatttgggt agtatatgct acccagatat aaattaggat     240
agcatatact accctaatct ctattaggat agcatatgct acccggatac agattaggat     300
agcatatact acccagatat agattaggat agcatatgct acccagatat agattaggat     360
agcctatgct acccagatat aaattaggat agcatatact acccagatat agattaggat     420
agcatatgct acccagatat agattaggat agcctatgct acccagatat agattaggat     480
agcatatgct atcc                                                       494

<210> SEQ ID NO 5
<211> LENGTH: 140
<212> TYPE: DNA
<213> ORGANISM: Human herpesvirus 4 (Epstein-Barr virus)
<220> FEATURE:
<223> OTHER INFORMATION: Origin of replication P (OriP) 'Dyad Symmetry'
      region

<400> SEQUENCE: 5
atcgctgttc cttaggaccc ttttactaac cctaattcga tagcatatgc ttcccgttgg      60
gtaacatatg ctattgaatt agggttagtc tggatagtat atactactac ccgggaagca     120
tatgctaccc gtttagggtt                                                 140

<210> SEQ ID NO 6
<211> LENGTH: 90
<212> TYPE: DNA
<213> ORGANISM: Artificial Sequence
<220> FEATURE:
<223> OTHER INFORMATION: DNA-binding site for EBNA-1

<400> SEQUENCE: 6
tggataataa gtgttgcctc gtgggtaacc gggcagcatg ctacctggat aataagtgtt      60
gcctcgtggg taaccgggca gcatgctacc                                      90

<210> SEQ ID NO 7
<211> LENGTH: 641
<212> TYPE: PRT
<213> ORGANISM: Human herpesvirus 4 (Epstein-Barr virus)
<220> FEATURE:
<223> OTHER INFORMATION: Epstein-Barr virus nuclear antigen 1

<400> SEQUENCE: 7

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80
```

-continued

```
Gly Cys Lys Gly Thr His Gly Thr Gly Ala Gly Ala Gly
                 85              90              95
Gly Ala Gly Ala Gly Ala Gly Ala Gly Gly Ala Gly Ala Gly
            100             105             110
Gly Gly Ala Gly Gly Ala Gly Gly Ala Gly Gly Ala Gly Gly
            115             120             125
Gly Ala Gly Ala Gly Gly Ala Gly Gly Ala Gly Gly Ala Gly Ala
        130             135             140
Gly Gly Gly Ala Gly Ala Gly Gly Ala Gly Gly Ala Gly Ala Gly
145             150             155             160
Gly Gly Ala Gly Gly Ala Gly Gly Ala Gly Gly Gly Ala Gly
            165             170             175
Ala Gly Gly Gly Ala Gly Gly Ala Gly Ala Gly Gly Ala Gly Gly
            180             185             190
Ala Gly Gly Ala Gly Ala Gly Gly Ala Gly Ala Gly Gly Ala Gly
            195             200             205
Gly Ala Gly Gly Ala Gly Ala Gly Gly Ala Gly Ala Gly Gly Ala
        210             215             220
Gly Gly Ala Gly Gly Ala Gly Ala Gly Gly Ala Gly Ala Gly Ala
225             230             235             240
Gly Ala Gly Gly Ala Gly Ala Gly Gly Ala Gly Gly Ala Gly Ala Gly
            245             250             255
Gly Ala Gly Gly Ala Gly Ala Gly Gly Ala Gly Gly Ala Gly Ala Gly
            260             265             270
Gly Gly Ala Gly Gly Ala Gly Ala Gly Gly Ala Gly Gly Ala Gly
        275             280             285
Ala Gly Gly Ala Gly Gly Ala Gly Ala Gly Gly Ala Gly Gly Ala Gly
        290             295             300
Ala Gly Gly Ala Gly Gly Ala Gly Ala Gly Gly Ala Gly Ala Gly
305             310             315             320
Gly Ala Gly Ala Gly Gly Gly Gly Arg Gly Arg Gly Ser Gly Gly
            325             330             335
Arg Gly Arg Gly Gly Ser Gly Gly Arg Gly Arg Gly Gly Ser Gly Gly
            340             345             350
Arg Arg Gly Arg Gly Arg Glu Arg Ala Arg Gly Gly Ser Arg Glu Arg
            355             360             365
Ala Arg Gly Arg Gly Arg Gly Arg Gly Glu Lys Arg Pro Arg Ser Pro
        370             375             380
Ser Ser Gln Ser Ser Ser Ser Gly Ser Pro Pro Arg Arg Pro Pro Pro
385             390             395             400
Gly Arg Arg Pro Phe Phe His Pro Val Gly Glu Ala Asp Tyr Phe Glu
            405             410             415
Tyr His Gln Glu Gly Gly Pro Asp Gly Glu Pro Asp Val Pro Pro Gly
            420             425             430
Ala Ile Glu Gln Gly Pro Ala Asp Asp Pro Gly Glu Gly Pro Ser Thr
            435             440             445
Gly Pro Arg Gly Gln Asp Gly Gly Arg Arg Lys Lys Gly Gly Trp
        450             455             460
Phe Gly Lys His Arg Gly Gln Gly Gly Ser Asn Pro Lys Phe Glu Asn
465             470             475             480
Ile Ala Glu Gly Leu Arg Ala Leu Leu Ala Arg Ser His Val Glu Arg
            485             490             495
```

```
Thr Thr Asp Glu Gly Thr Trp Val Ala Gly Val Phe Val Tyr Gly Gly
            500                 505                 510
Ser Lys Thr Ser Leu Tyr Asn Leu Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640
Glu

<210> SEQ ID NO 8
<211> LENGTH: 417
<212> TYPE: PRT
<213> ORGANISM: Artificial Sequence
<220> FEATURE:
<223> OTHER INFORMATION: truncated form of Epstein-Barr virus nuclear
      antigen 1

<400> SEQUENCE: 8

Met Ser Asp Glu Gly Pro Gly Thr Gly Pro Gly Asn Gly Leu Gly Glu
1               5                   10                  15
Lys Gly Asp Thr Ser Gly Pro Glu Gly Ser Gly Gly Ser Gly Pro Gln
            20                  25                  30
Arg Arg Gly Gly Asp Asn His Gly Arg Gly Arg Gly Arg Gly Arg Gly
        35                  40                  45
Arg Gly Gly Gly Arg Pro Gly Ala Pro Gly Gly Ser Gly Ser Gly Pro
    50                  55                  60
Arg His Arg Asp Gly Val Arg Arg Pro Gln Lys Arg Pro Ser Cys Ile
65                  70                  75                  80
Gly Cys Lys Gly Thr His Gly Gly Thr Gly Ala Gly Ala Gly Ala Gly
                85                  90                  95
Gly Ala Gly Ala Gly Gly Gly Gly Arg Gly Gly Gly Ser Gly Gly
            100                 105                 110
Arg Gly Arg Gly Gly Ser Gly Gly Arg Gly Arg Gly Gly Ser Gly Gly
        115                 120                 125
Arg Arg Gly Arg Gly Arg Glu Arg Ala Arg Gly Gly Ser Arg Glu Arg
    130                 135                 140
Ala Arg Gly Arg Gly Arg Gly Arg Gly Glu Lys Arg Pro Arg Ser Pro
145                 150                 155                 160
Ser Ser Gln Ser Ser Ser Ser Gly Ser Pro Pro Arg Arg Pro Pro Pro
                165                 170                 175
Gly Arg Arg Pro Phe Phe His Pro Val Gly Glu Ala Asp Tyr Phe Glu
            180                 185                 190
Tyr His Gln Glu Gly Gly Pro Asp Gly Glu Pro Asp Val Pro Pro Gly
        195                 200                 205
```

```
Ala Ile Glu Gln Gly Pro Ala Asp Asp Pro Gly Glu Gly Pro Ser Thr
    210                 215                 220

Gly Pro Arg Gly Gln Gly Asp Gly Gly Arg Arg Lys Lys Gly Gly Trp
225                 230                 235                 240

Phe Gly Lys His Arg Gly Gln Gly Gly Ser Asn Pro Lys Phe Glu Asn
                245                 250                 255

Ile Ala Glu Gly Leu Arg Ala Leu Leu Ala Arg Ser His Val Glu Arg
                260                 265                 270

Thr Thr Asp Glu Gly Thr Trp Val Ala Gly Val Phe Val Tyr Gly Gly
            275                 280                 285

Ser Lys Thr Ser Leu Tyr Asn Leu Arg Arg Gly Thr Ala Leu Ala Ile
    290                 295                 300

Pro Gln Cys Arg Leu Thr Pro Leu Ser Arg Leu Pro Phe Gly Met Ala
305                 310                 315                 320

Pro Gly Pro Gly Pro Gln Pro Gly Pro Leu Arg Glu Ser Ile Val Cys
                325                 330                 335

Tyr Phe Met Val Phe Leu Gln Thr His Ile Phe Ala Glu Val Leu Lys
                340                 345                 350

Asp Ala Ile Lys Asp Leu Val Met Thr Lys Pro Ala Pro Thr Cys Asn
            355                 360                 365

Ile Arg Val Thr Val Cys Ser Phe Asp Asp Gly Val Asp Leu Pro Pro
    370                 375                 380

Trp Phe Pro Pro Met Val Glu Gly Ala Ala Ala Glu Gly Asp Asp Gly
385                 390                 395                 400

Asp Asp Gly Asp Glu Gly Gly Asp Gly Asp Glu Gly Glu Glu Gly Gln
                405                 410                 415

Glu

<210> SEQ ID NO 9
<211> LENGTH: 152
<212> TYPE: PRT
<213> ORGANISM: Cricetulus griseus (Chinese hamster)
<220> FEATURE:
<223> OTHER INFORMATION: nucleoside diphosphate kinase A

<400> SEQUENCE: 9

Met Ala Asn Ser Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Ile Asp Leu Lys Asp Arg Pro Phe Phe Thr Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
        115                 120                 125

Glu Ile Gly Leu Trp Phe Gln Pro Glu Glu Leu Val Asp Tyr Lys Ser
    130                 135                 140

Cys Ala Gln Asn Trp Ile Tyr Glu
```

<210> SEQ ID NO 10
<211> LENGTH: 35
<212> TYPE: DNA
<213> ORGANISM: Artificial Sequence
<220> FEATURE:
<223> OTHER INFORMATION: oligonucleotide primer fwd-eGFP

<400> SEQUENCE: 10
tatgctagcg gtaccatggt gagcaagggc gagga    35

<210> SEQ ID NO 11
<211> LENGTH: 35
<212> TYPE: DNA
<213> ORGANISM: Artificial Sequence
<220> FEATURE:
<223> OTHER INFORMATION: oligonucleotide primer rev-eGFP

<400> SEQUENCE: 11
ataagatctg gtaccttgt acagctcgtc catgc    35

<210> SEQ ID NO 12
<211> LENGTH: 35
<212> TYPE: DNA
<213> ORGANISM: Artificial Sequence
<220> FEATURE:
<223> OTHER INFORMATION: oligonucleotide primer fwd-EBNA

<400> SEQUENCE: 12
tattctagaa tgtctgacga ggggccaggt acagg    35

<210> SEQ ID NO 13
<211> LENGTH: 31
<212> TYPE: DNA
<213> ORGANISM: Artificial Sequence
<220> FEATURE:
<223> OTHER INFORMATION: oligonucleotide primer rev-EBNA

<400> SEQUENCE: 13
ataaccggtt cactcctgcc cttcctcacc c    31

<210> SEQ ID NO 14
<211> LENGTH: 22
<212> TYPE: DNA
<213> ORGANISM: Artificial Sequence
<220> FEATURE:
<223> OTHER INFORMATION: oligonucleotide primer fwd-NDPK-A

<400> SEQUENCE: 14
tatggcgcgc catggccaac at    22

<210> SEQ ID NO 15
<211> LENGTH: 39
<212> TYPE: DNA
<213> ORGANISM: Artificial Sequence
<220> FEATURE:
<223> OTHER INFORMATION: oligonucleotide primer rev-NDPK-A

<400> SEQUENCE: 15
atactcgagt cactcataga tccagttttg tgcacagct    39

MAMMALIAN EXPRESSION SYSTEM

CROSS-REFERENCE TO RELATED APPLICATIONS

This application is a 371 of PCT/EP2016/070083, filed Aug. 25, 2016, which claims benefit of European Patent Application No. 15182412.5 filed on Aug. 25, 2015.

REFERENCE TO SEQUENCE LISTING SUBMITTED ELECTRONICALLY VIA EFS-WEB

The content of the electronically submitted sequence listing, file name: ST25_SubstituteSequenceListing.txt; size: 32,293 bytes; and date of creation: May 7, 2020, filed herewith, is incorporated herein by reference in its entirety.

FIELD OF THE INVENTION

The present invention relates to mammalian expression system being particularly suitable for the high-yield production of recombinant proteins. More specifically, the expression system combines the use of nucleoside diphosphate kinase A for enhancing DNA transfection efficacy and DNA nuclear delivery and Epstein Barr nuclear antigen-1 for improving extrachromosomal maintenance of the transfected DNA.

BACKGROUND

Recombinant (poly)peptides and proteins for applications in basic research, diagnostics, and therapy, such as antibody molecules, vaccines, hormones, and growth factors, are produced using a wide variety of genetically engineered organisms that include both prokaryotic and eukaryotic cells. However, the vast majority of recombinant peptides or proteins include post-translational modifications that cannot be mimicked or re-produced when using prokaryotic host cells. For this reason, mammalian gene expression systems have turned out to represent a preferred choice.

Mammalian expression systems are widely used in production of recombinant protein. Apart from lymphoid cell lines, Chinese hamster ovary (CHO) cells represent one of the few cell types allowing for simple and efficient high-density suspension batch culture of mammalian cells. However, the use of CHO cells results in higher product yields, while lymphoid cells are more difficult to culture at an industrial scale.

Typically, in order to accomplish satisfying yields of recombinant peptides or proteins the methodological approach employed relies upon lengthy selection, screening and adaptation procedures to generate stably expressing recombinant cell lines.

On the other hand, generation of stable cell lines is not ideal in early drug development when it may be necessary to evaluate numerous potential therapeutic candidates. As an alternative to constructing stable cell lines, transient gene expression provides a means to rapidly generate recombinant proteins for such studies. However, limitation in transient expression technologies derive from the inability of mammalian cells to replicate and transfer plasmid DNA across generations and from inefficient DNA translocation from the cytosol into the nucleus.

In addition, given the considerable costs for recombinant production of polypeptides and proteins (both with stable and transient expression systems), it is also of utmost importance to maximize the yield of recombinant protein per bioreactor run. Process parameters that have considerable impact on product yield include inter alia the cell culture conditions, the copy number of the nucleic acids (genes) to be expressed, the efficiency with which these genes are transcribed and the corresponding mRNAs are translated, the stability of the mRNA, and the like.

Various attempts have yet been made in order to improve the yields of mammalian expression systems. One approach to particularly enhance transient expression is based on extrachromosomal maintenance of the transfected genetic constructs by using Epstein Barr virus nuclear antigen 1 (EBNA-1), a nuclear phosphoprotein that binds with high affinity to three major DNA sites within the Epstein Barr virus genome and plays an important role in virus replication. One such binding site resides in the OriP (origin of replication P) sequence of Epstein Barr virus, which is employed in some available expression systems as complementary cis-element to EBNA-1, thus enabling maintenance and replication of episomal elements (such as vectors) in a transfected host cell. Exemplary such EBNA-1 based mammalian expression systems are described inter alia in U.S. Pat. No. 7,294,505 B2, US patent publication 2005/0260564 A1, European patent 1 945 781 B1, and international patent publication WO 2009/137911 A1. However, these systems are still hampered by an inefficient translocation of the transfected DNA to the nucleus of the host cell.

Hence, there still remains a need for improved mammalian gene expression systems resulting in high yields of the recombinant polypeptides or proteins produced. In particular, there is a need for mammalian gene expression systems that overcome the above-mentioned limitations.

Accordingly, it is an object of the present invention to provide such a mammalian expression system, primarily suitable expression constructs and corresponding mammalian host cells.

SUMMARY OF THE INVENTION

In one aspect, the present invention relates to an expression system for the heterologous expression of a nucleic acid sequence of interest in a mammalian cell, the system comprising: (i) a first genetic entity, comprising: a nucleic acid sequence encoding a functional Epstein Barr virus nuclear antigen 1 (EBNA-1), the nucleic acid sequence being operably linked to regulatory elements that allow for expression of the nucleic acid sequence encoding a functional EBNA-1; (ii) a second genetic entity, comprising: a nucleic acid sequence encoding a functional nucleoside diphosphate kinase A (NDPK-A), the nucleic acid sequence being operably linked to regulatory elements that allow for expression of the nucleic acid sequence encoding a functional NDPK-A; (iii) a third genetic entity, comprising: the nucleic acid sequence of interest being operably linked to regulatory elements that allow for expression of the nucleic acid sequence of interest; and (iv) a fourth genetic entity, comprising: the Epstein Barr virus origin of replication P (OriP) sequence or one or more subsequences thereof, wherein the one or more subsequences comprise at least the 'Family of Repeats' DNA-binding site for EBNA-1 and the 'Dyad Symmetry' DNA-binding site for EBNA-1.

In a preferred embodiment, any one or more of the first genetic entity, the second genetic entity, the third genetic entity, and the fourth genetic entity are capable of independent replication.

In a further preferred embodiment, any one or more of the first genetic entity, the second genetic entity, the third genetic entity, and the fourth genetic entity are comprised in one or more vectors. In a particularly preferred embodiment, (a) the first genetic entity and the second genetic entity are comprised in a first vector; and (b) the third genetic entity and the fourth genetic entity are comprised in a second vector, and particularly wherein the first vector does not encompass a functional Epstein Barr virus OriP sequence, and the second vector does not encompass a nucleic acid sequence encoding a functional EBNA-1.

In specific embodiments, the expression system is further characterized by any one or more of the following structural features: (a) the nucleic acid sequence encoding a functional EBNA-1 is selected from the group of sequences consisting of SEQ ID NO: 1 and SEQ ID NO: 2; (b) the nucleic acid sequence encoding a functional NDPK-A has the sequence of SEQ ID NO: 3; (c) the nucleic acid sequence encoding the 'Family of Repeats' DNA-binding site for EBNA-1 has the sequence of SEQ ID NO: 4 and the nucleic acid sequence encoding the 'Dyad Symmetry' DNA-binding site for EBNA-1 has the sequence of SEQ ID NO: 5; and (d) the expression system further comprises at least one nucleic acid sequence encoding a selection marker, the selection marker particularly being glutamine synthase In a further specific embodiment, the nucleic acid sequence of interest encodes an antibody or an antibody fragment.

In another aspect, the present invention relates to a mammalian host cell comprising the expression system as defined herein. Preferably, the host cell is a CHO cell, and particularly a CHO cell lacking glutamine synthase.

In a further aspect, the present invention relates to a method for the production of the mammalian host cell as defined herein, comprising: (i) providing a mammalian cell; (ii) transfecting the mammalian cell with any one or more of the first genetic entity, the second genetic entity, the third genetic entity, and the fourth genetic entity as defined herein; and (iii) transfecting the mammalian cell obtained in (ii) with the remaining any one or more of the first genetic entity, the second genetic entity, the third genetic entity, and the fourth genetic entity as defined herein.

In a specific embodiment of the method, step (ii) further comprises: selecting a mammalian cell stably transfected with the any one or more of the first genetic entity, the second genetic entity, the third genetic entity, and the fourth genetic entity.

In a further aspect, the present invention relates to a kit-of-parts for the production of the mammalian host cell as defined herein, comprising: (i) a mammalian cell; and (ii) a first genetic entity, a second genetic entity, a third genetic entity, and a fourth genetic entity as defined herein.

In yet a further aspect, the present invention relates to a method for the expression of a nucleic acid sequence of interest in a mammalian cell, comprising: (i) transfecting a mammalian cell with any one or more of the first genetic entity, the second genetic entity, the third genetic entity, and the fourth genetic entity as defined herein; (ii) transfecting the mammalian cell obtained in (i) with the remaining any one or more of the first genetic entity, the second genetic entity, the third genetic entity, and the fourth genetic entity as defined herein; and (iii) culturing the mammalian cell obtained in (ii) under conditions allowing for the expression of the nucleic acid sequence of interest.

In a specific embodiment, step (i) and/or step (ii) comprise(s) a stable transfection. In another specific embodiment, step (i) and/or step (ii) comprise(s) a transient transfection.

In yet a further aspect, the present invention relates to the use of an expression system as defined herein as molecular tool for enhancing heterologous nucleic acid expression in mammalian cells.

Other embodiments of the present invention will become apparent from the detailed description hereinafter.

DETAILED DESCRIPTION OF THE INVENTION

Figure 1:
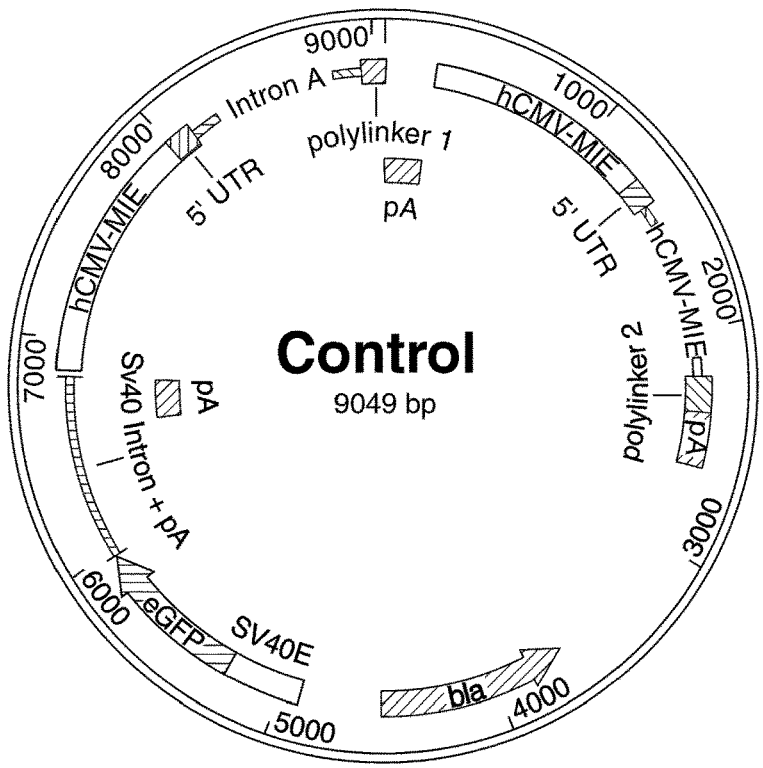
FIG. 1 schematically illustrates exemplary expression vectors generated for transient transfection studies. All vectors encompass the gene encoding the enhanced green fluorescent protein (eGFP) as selection marker. (A) Control vector. (B) Vector including the 'Family of Repeats' and 'Dyad Symmetry' DNA-binding sites for the Epstein Barr nuclear antigen 1 (EBNA-1) derived from the OriP sequence of Epstein Barr virus ("Ori P"). (C) Vector including the Ori P sequences and a nucleic acid sequence encoding EBNA-1. (D) Vector including a nucleic acid sequence encoding nucleoside diphosphate kinase A (NDPK-A). Images prepared by using the SnapGene software.
Figure 1:
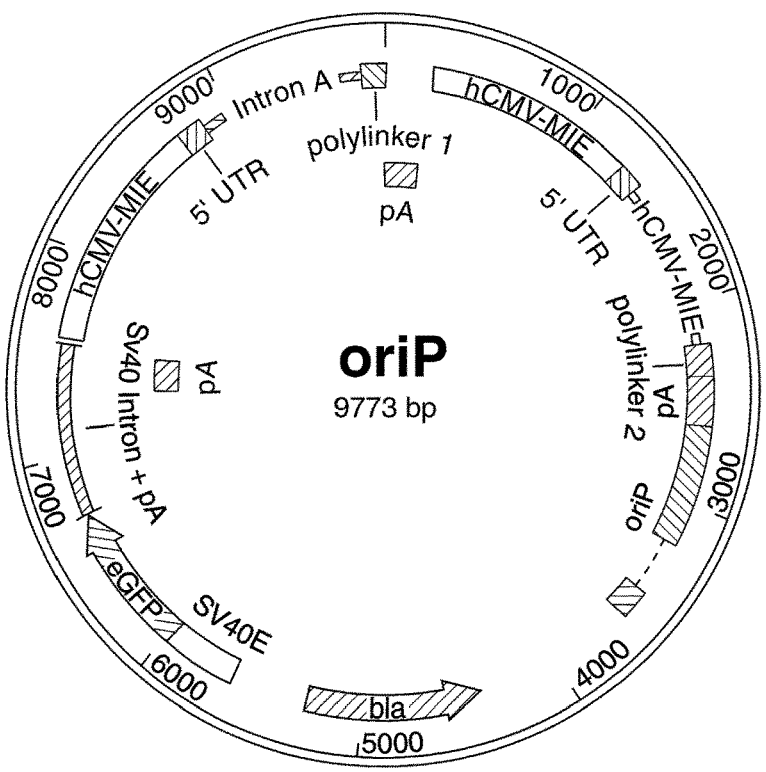
Figure 1:
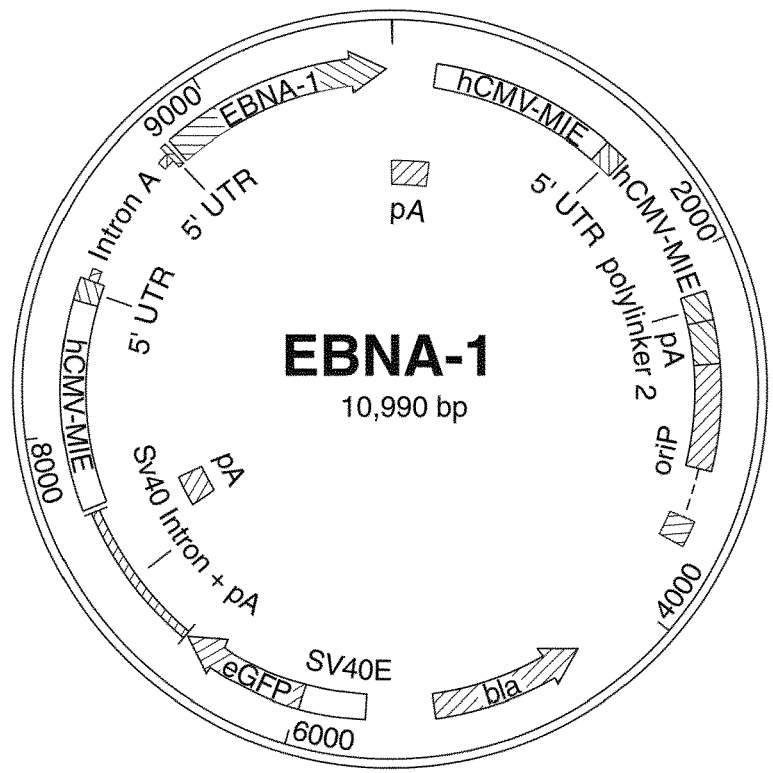
Figure 1:
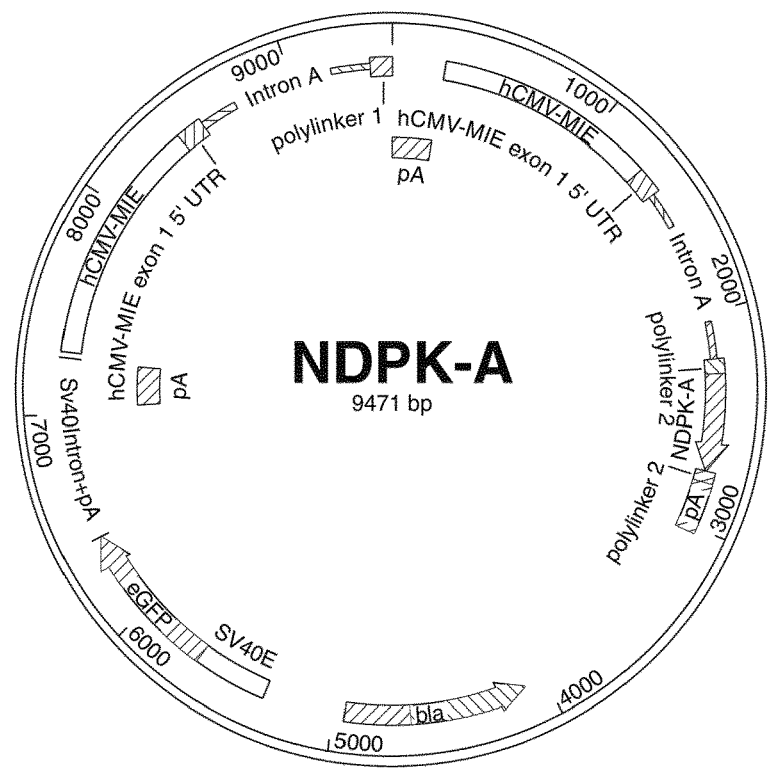
Figure 2:
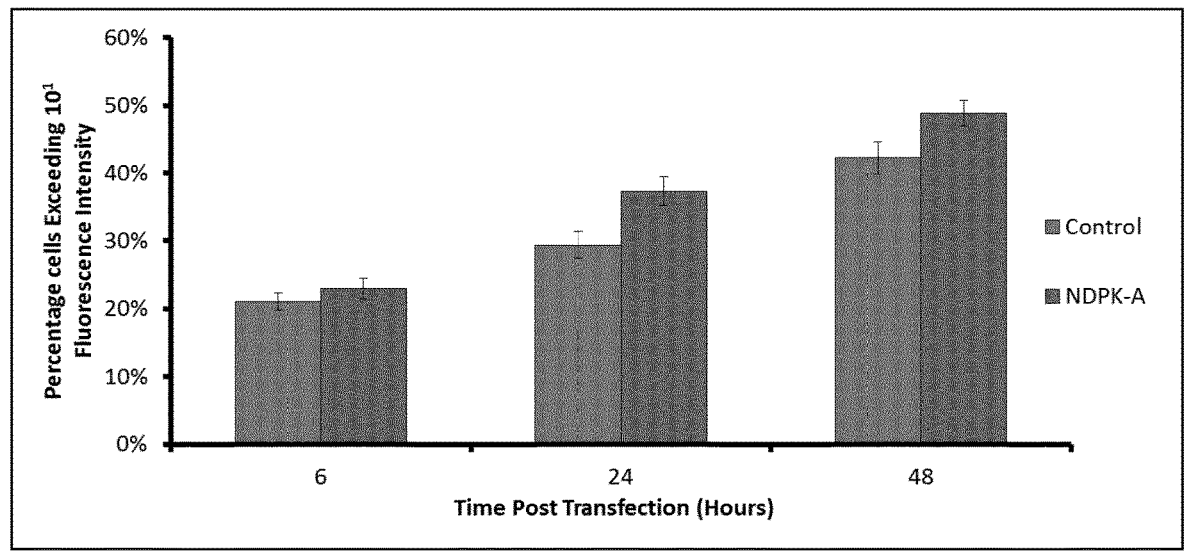
FIG. 2 illustrates the effect of using nucleoside diphosphate kinase A (NDPK-A) in order to enhance DNA delivery to the nucleus in Chinese hamster ovary (CHO) cells. The cells were transiently transfected with a control vector encompassing a nucleic acid sequence encoding the enhanced green fluorescent protein (eGFP) as reporter and a "test" vector additionally encompassing a nucleic acid sequence encoding the hamster NDPK-A protein, respectively. Shown is the percentage of CHO cells expressing the eGFP gene after 6, 24, and 48 hours post-transfection with the respective two expression vectors using different fluorescence intensity thresholds: (A) $10^1$, (B) $10^2$, and (C) $10^3$. Data represent means±SEM of three independent experiments. At all three points in time, for each intensity threshold, the construct encompassing the NDPK-A gene shows an increased number of cells expressing eGFP as compared to the control construct. The increase in mean fluorescence is shown in (D).
Figure 2:
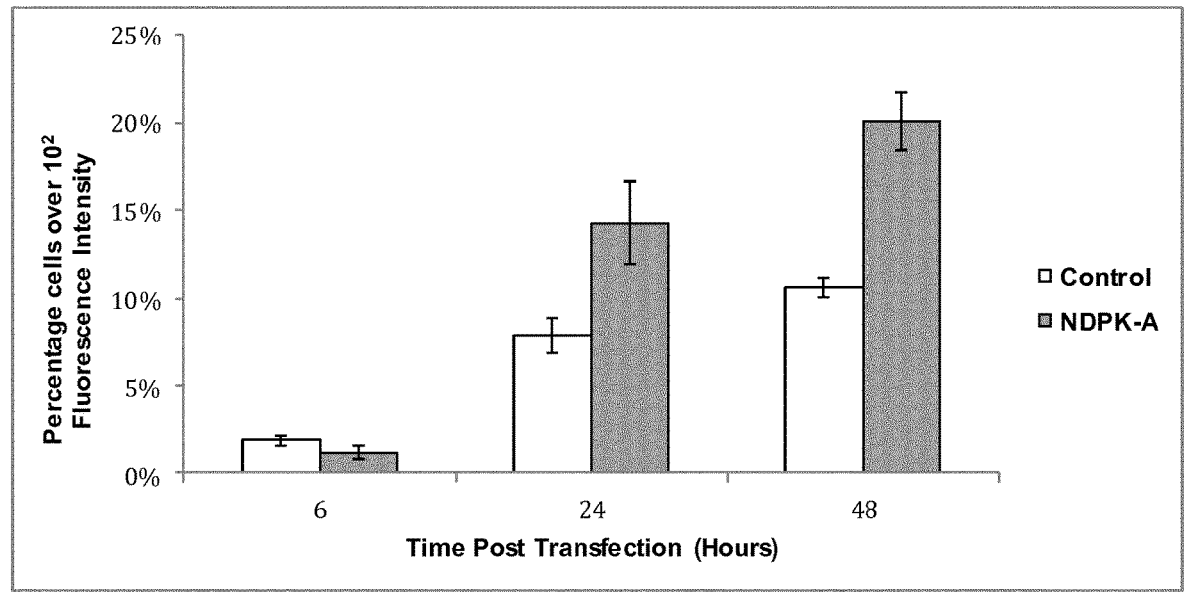
Figure 2:
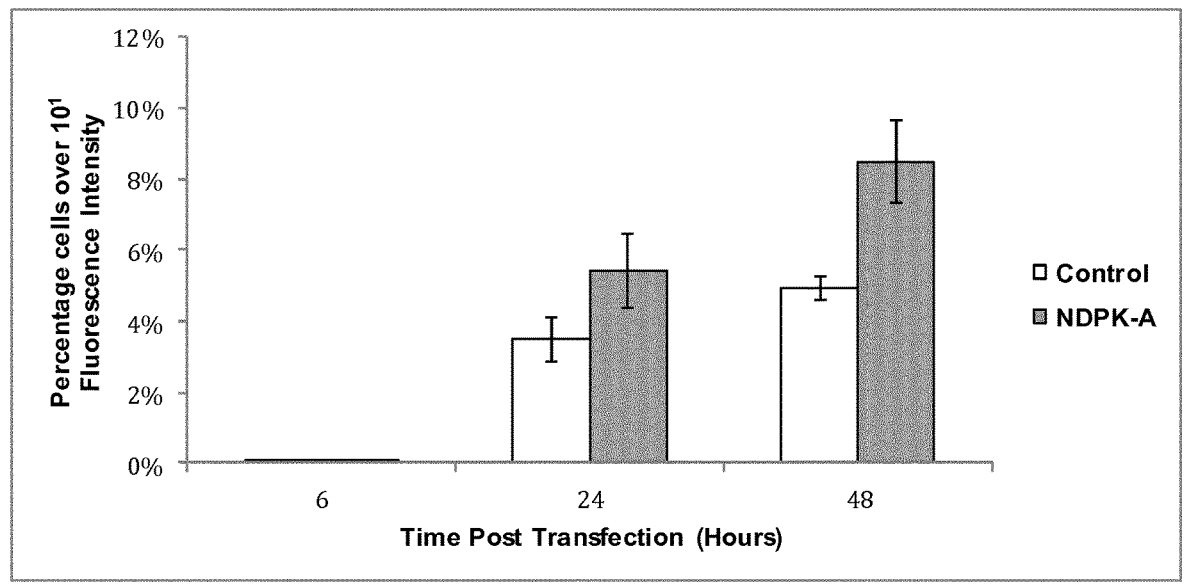
Figure 2:
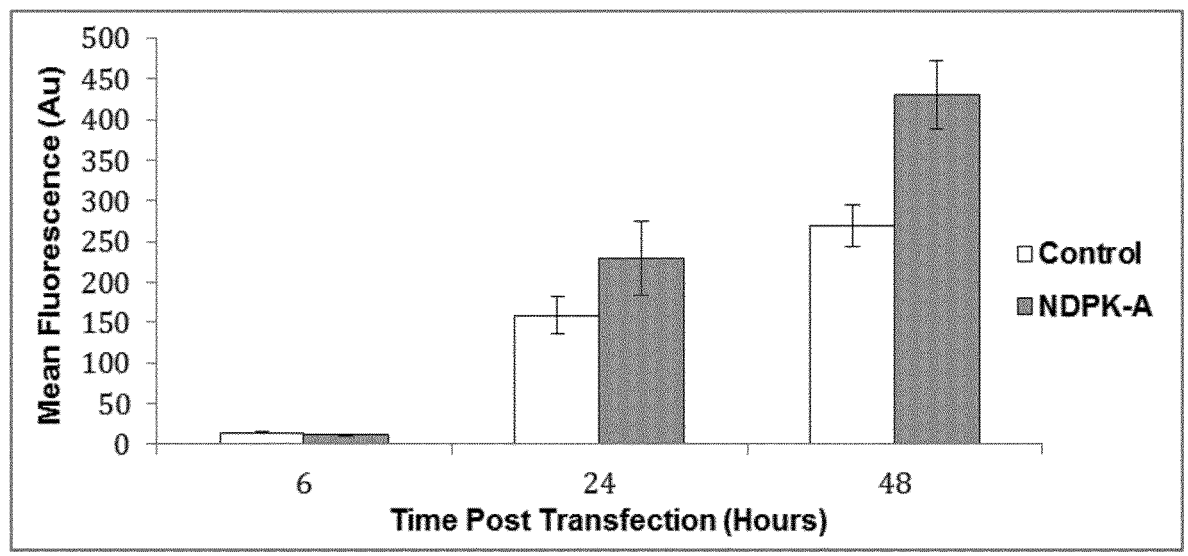
Figure 3:
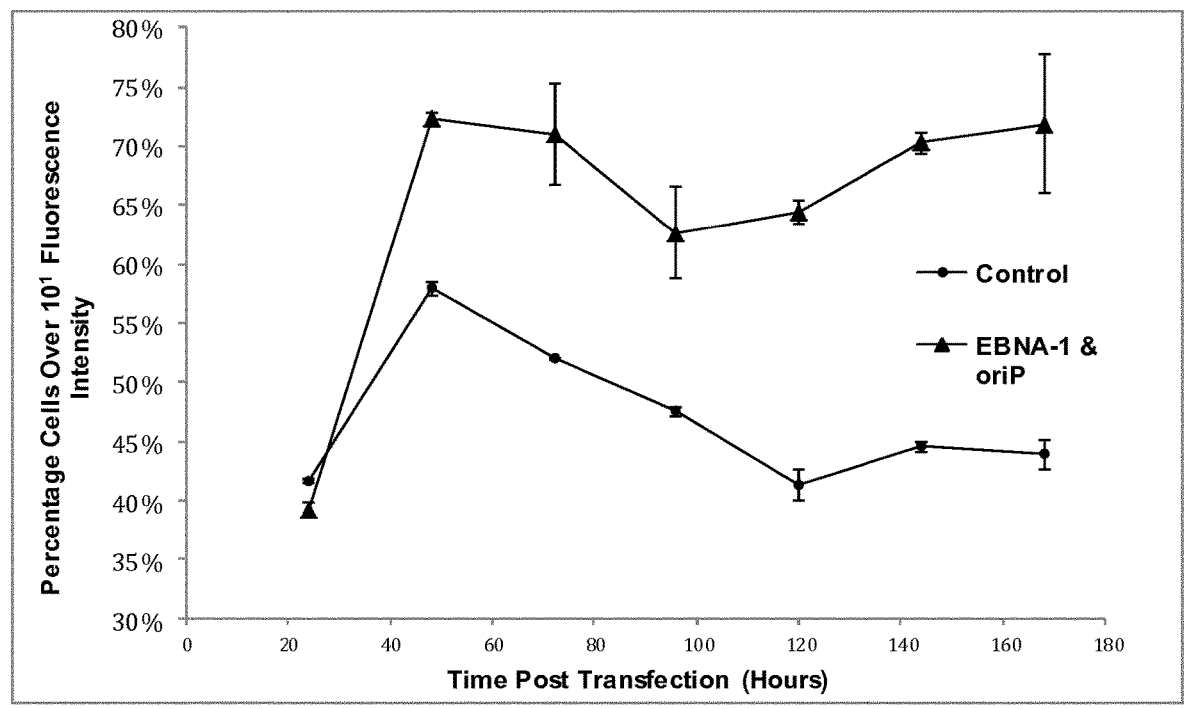
FIG. 3 illustrates the effect of using Epstein Barr nuclear antigen 1 (EBNA-1) and Epstein Barr virus OriP sequences in order to induce extrachromosomal maintenance of transfected vector DNA in Chinese hamster ovary (CHO) cells. The cells were transiently transfected with a control vector encompassing a nucleic acid sequence encoding the enhanced green fluorescent protein (eGFP) as reporter; and a "test" vector additionally encompassing a nucleic acid sequence encoding the EBNA-1 as well as the 'Family of Repeats' and 'Dyad Symmetry' EBNA-1 DNA-binding site of the OriP (origin of replication P) sequence. Shown is the percentage of CHO cells expressing the eGFP gene at various time points 24 to 168 hours post-transfection with the respective two expression vectors using different fluorescence intensity thresholds: (A) $10^1$, (B) $10^2$, and (C) $10^3$. Data represent means±SEM of three independent experiments. After 24 hours post-transfection the expression levels were fairly comparable but at all other points in time, the construct encompassing the EBNA-1 gene and OriP sequences shows an increased number of cells expressing eGFP as compared to the control construct. The increase in mean fluorescence is shown in (D).
Figure 3:
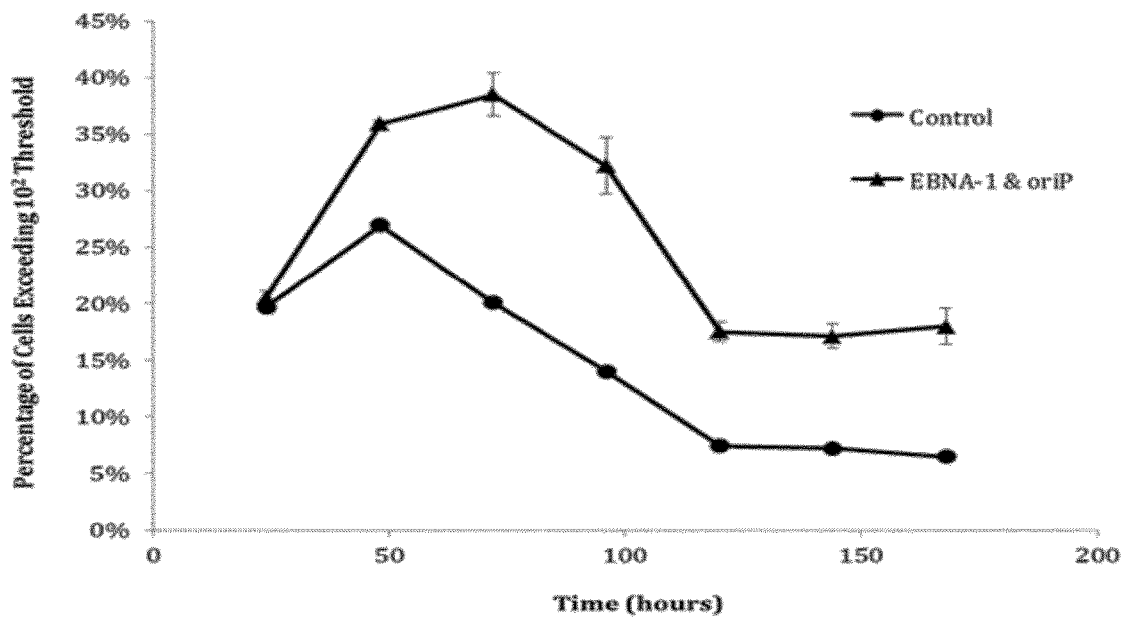
Figure 3:
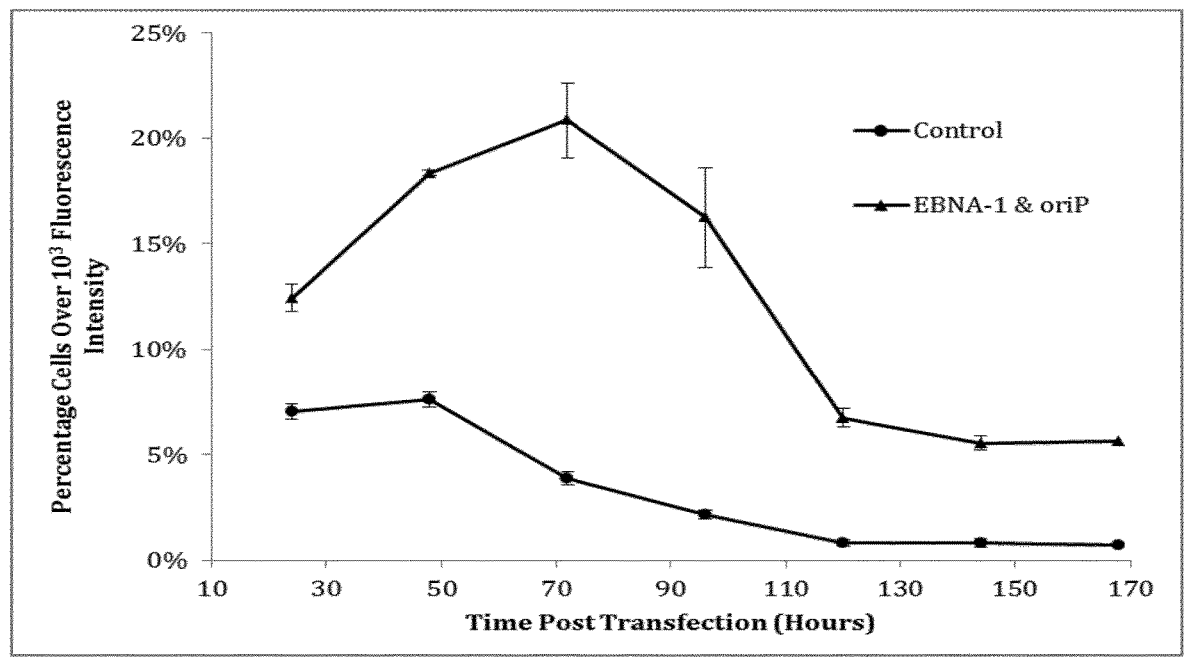
Figure 3:
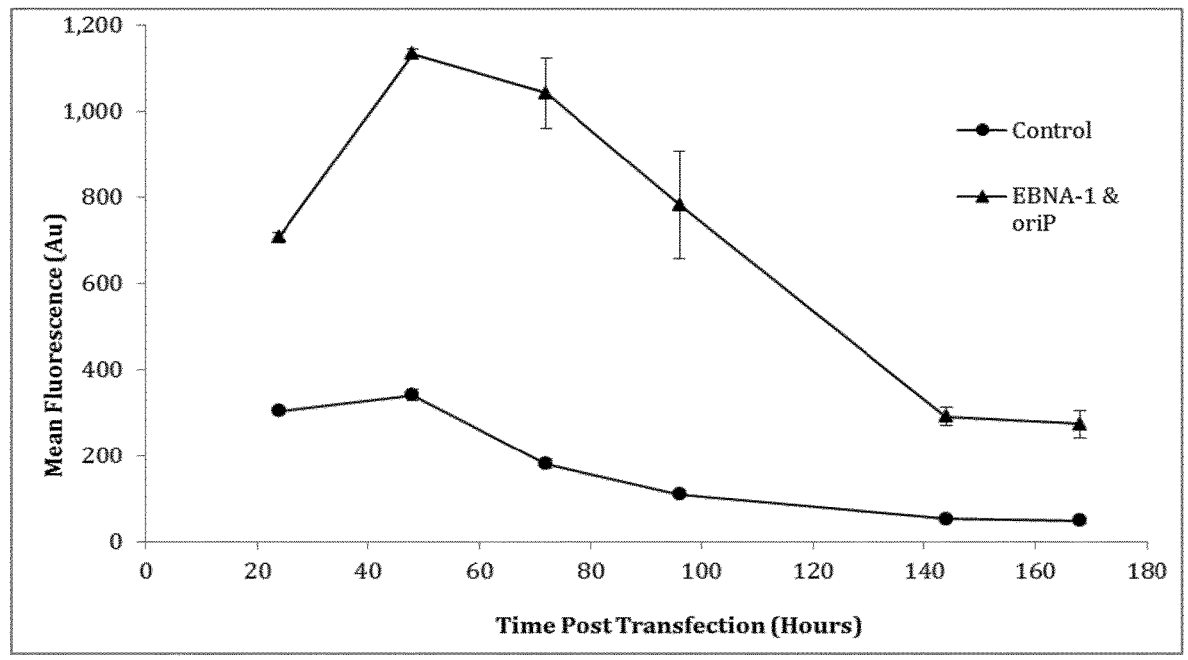

The present invention is based on the unexpected finding that the combined use in an expression system of nucleoside diphosphate kinase A (NDPK-A) and Epstein Barr nuclear antigen-1 (EBNA-1) synergistically enhance heterologous gene expression in mammalian cells. The use of the nuclear shuttle protein NDPK-A resulted in an improvement of transfection efficiency and an increase in the DNA copy number delivered to the nucleus of mammalian cells. Furthermore, EBNA-1, particularly coupled with complementary OriP (origin of replication P) elements, was employed to induce extra-chromosomal maintenance. The combination of these functional genetic elements resulted in an expression system by which (transiently) transfected DNA is tethered to the host chromosome and is thus simultaneously replicated during cell division leaving plasmid copies in each of the divided cells, thereby reducing dilution of the transfected DNA from one generation to the next and, in turn, synergistically enhancing yields of recombinant proteins produced.

The present invention illustratively described in the following may suitably be practiced in the absence of any element or elements, limitation or limitations, not specifically disclosed herein.

Where the term "comprising" is used in the present description and the claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g., "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to an expression system for the heterologous expression of a nucleic acid sequence of interest in a mammalian cell, the system comprising:
(i) a first genetic entity, comprising: a nucleic acid sequence encoding a functional Epstein Barr virus nuclear antigen 1 (EBNA-1), the nucleic acid sequence being operably linked to regulatory elements that allow for expression of the nucleic acid sequence encoding a functional EBNA-1;
(ii) a second genetic entity, comprising: a nucleic acid sequence encoding a functional nucleoside diphosphate kinase A (NDPK-A), the nucleic acid sequence being operably linked to regulatory elements that allow for expression of the nucleic acid sequence encoding a functional NDPK-A;
(iii) a third genetic entity, comprising: the nucleic acid sequence of interest being operably linked to regulatory elements that allow for expression of the nucleic acid sequence of interest; and
(iv) a fourth genetic entity, comprising: the Epstein Barr virus origin of replication P (OriP) sequence or one or more subsequences thereof, wherein the one or more subsequences comprise at least the 'Family of Repeats' DNA-binding site for EBNA-1 and the 'Dyad Symmetry' DNA-binding site for EBNA-1.

The term "heterologous expression", as used herein, refers to the expression (i.e. its transcription into mRNA and subsequent translation in an amino acid sequence) of a nucleic acid sequence of interest in a host cell that does not naturally express this nucleic acid sequence. Heterologous expression is typically accomplished by means of recombinant DNA technology.

The term "genetic entity", as used herein, generally denotes a genetic construct in form of a nucleic acid sequence encompassing the respective functional elements described herein above.

Whenever reference is made to "regulatory elements", as used herein, this denotes the presence of regulatory elements being located 5' ("upstream") or 3' ("downstream") or preferably 5' and 3' of the nucleic acid sequence to which they are operably linked and thus allowing for the expression of this nucleic acid sequence (cf. also below).

Any one or more of the first genetic entity, the second genetic entity, the third genetic entity, and the fourth genetic entity referred to above may be comprised in or represent a linear construct (i.e. a nucleic acid molecule having free 5'- and 3'-termini) such as an expression cassette that can be integrated into the host cell's genome via genetic recombination. Such recombination may either occur at random positions of the genome by non-homologous recombination or at specific positions of the genome by homologous recombination or via site-specific integrases. The skilled person is well aware of genetically engineering such constructs in order to allow for recombination, for example by inserting long terminal repeat (LTR) sequences. All corresponding methods are well established in the art and can be derived from standard textbooks, such as, Sambrook, J., and Russel, D. W. (2001) *Molecular cloning: A laboratory manual* (3rd Ed.), Cold Spring Harbor Laboratory Press, Cold Spring Harbor, N.Y.; and Ausubel, F. M. et al. (2001) *Current Protocols in Molecular Biology*, Wiley & Sons, Hoboken, N.J. Typically, such linear constructs are not capable of independent replication, that is, to propagate the encoded genetic information without becoming integrated into the host cell's genome.

In certain embodiments, any one of the first genetic entity, the second genetic entity, the third genetic entity, and the fourth genetic entity is comprised in or represents a linear construct (i.e., the first, the second, the third, or the fourth), which may become (or be) integrated in the genome of the host cell being transfected. The remaining respective three genetic entities may be comprised in or represent one or more other linear construct(s). In certain other embodiments, any two of the first genetic entity, the second genetic entity, the third genetic entity, and the fourth genetic entity are comprised in or represent the same linear construct (i.e., the first and second, the first and third, the first and fourth, the second and third, the second and fourth, or the third and fourth, each in any order with regard to each other), which may become (or be) integrated in the genome of the host cell being transfected. The remaining respective two genetic entities may be comprised in or represent one or two other linear construct(s). In certain other embodiments, any three of the first genetic entity, the second genetic entity, the third genetic entity, and the fourth genetic entity are comprised in or represent the same linear construct (i.e., the first and second and third, the first and second and fourth, the first and third and fourth, or the second and third and fourth, each in any order with regard to each other), which may become (or be) integrated in the genome of the host cell being transfected. The remaining respective genetic entity may be comprised in or represent another linear construct. In another embodiment, all four of the first genetic entity, the second genetic entity, the third genetic entity, and the fourth genetic entity are comprised in or represent the same linear construct), which may become (or be) integrated in the genome of the host cell being transfected.

On the other hand, the genetic entity may be comprised in or represent a circularly closed construct (i.e. a nucleic acid molecule not having free 5'- and 3'-termini) that may be further folded into a particular configuration. Examples of such constructs include any cloning vehicles known in the art, such as inter alia vectors, plasmids, cosmids, phagemids, viruses, bacteriophages, bacterial artificial chromosomes, yeast artificial chromosomes, with vectors being preferred. Typically, such circular constructs are capable of independent replication, that is, to maintain and propagate the encoded genetic information episomally (i.e., without a requirement to become integrated into the host cell's genome).

In preferred embodiments, any one or more (i.e. any two, any three or all four) of the first genetic entity, the second genetic entity, the third genetic entity, and the fourth genetic entity are capable of independent replication. Thereby, the respective genetic entities may be comprised in one or more circularly closed construct(s). Particularly preferably, any one or more (i.e. any two, any three or all four) of the first genetic entity, the second genetic entity, the third genetic entity, and the fourth genetic entity are comprised in one or more vectors.

In certain preferred embodiments, any one of the first genetic entity, the second genetic entity, the third genetic entity, and the fourth genetic entity is comprised in a circular construct, preferably a vector (i.e., the first, the second, the third, or the fourth). The remaining respective three genetic entities may be comprised in one or more other circular construct(s), preferably vector(s). In certain other preferred embodiments, any two of the first genetic entity, the second genetic entity, the third genetic entity, and the fourth genetic entity are comprised in the same circular construct, preferably the same vector (i.e., the first and second, the first and third, the first and fourth, the second and third, the second and fourth, or the third and fourth, each in any order with regard to each other). The remaining respective two genetic entities may be comprised in one or two other circular construct(s), preferably vector(s). In certain other preferred embodiments, any three of the first genetic entity, the second genetic entity, the third genetic entity, and the fourth genetic entity are comprised in the same circular construct, preferably the same vector (i.e., the first and second and third, the first and second and fourth, the first and third and fourth, or the second and third and fourth, each in any order with regard to each other). The remaining respective genetic entities may be comprised in another circular construct, preferably another vector. In another preferred embodiment, all four of the first genetic entity, the second genetic entity, the third genetic entity, and the fourth genetic entity are comprised in the same circular construct, preferably the same vector.

In certain other embodiments, any one of the first genetic entity, the second genetic entity, the third genetic entity, and the fourth genetic entity is comprised in or represents a linear construct, whereas the remaining respective three genetic entities are comprised in one or more circular construct(s). In certain other embodiments, any two of the first genetic entity, the second genetic entity, the third genetic entity, and the fourth genetic entity are comprised in or represent one or two linear construct(s), whereas the remaining respective two genetic entities are comprised in one or two circular construct(s). In certain other embodiments, any three of the first genetic entity, the second genetic entity, the third genetic entity, and the fourth genetic entity are comprised in or represent one or more linear construct(s), whereas the remaining respective genetic entity is comprised in a circular construct.

In a preferred embodiment, the expression system comprises: (a) a first vector comprising the first genetic entity and the second genetic entity; and (b) a second vector comprising the third genetic entity and the fourth genetic entity. Particularly preferably, the first vector does not encompass a functional Epstein Barr virus OriP sequence, and the second vector does not encompass a nucleic acid sequence encoding a functional Epstein Barr virus nuclear antigen 1 (EBNA-1).

A "functional Epstein Barr virus (EBV) origin of replication P (OriP) sequence", as used herein, denotes an OriP sequence exhibiting the same or substantially the same functionality as in EBV. Preferably, no EBV derived nucleic acid sequence at all is comprised. The OriP sequence region of EBV is well known in the art (Hudson, G. S. et al. (1985) *Virology* 147, 81-98; Reisman, D. et al. (1985) *Mol. Cell. Biol.* 5, 1822-1832) and described in more detail below as well as the meaning of the term "functional EBNA-1."

In a further particular embodiment, the first vector of the expression system does not comprise any nuclear localization sequences (NLS) for targeting the functional nucleoside diphosphate kinase A (NDPK-A) to the nucleus of the host cell.

In a further particular embodiment, the expression system comprises: (a) a first vector comprising the first genetic entity and the third genetic entity; and (b) a second vector comprising the second genetic entity and the fourth genetic entity. Particularly, the first vector does not encompass a functional Epstein Barr virus OriP sequence, and the second vector does not encompass a nucleic acid sequence encoding a functional EBNA-1.

In yet a further particular embodiment, the expression system comprises: (a) a first vector comprising the second genetic entity and the third genetic entity; and (b) a second vector comprising the first genetic entity and the fourth genetic entity. Particularly, the first vector does not encompass a functional Epstein Barr virus OriP sequence and does not encompass a nucleic acid sequence encoding a functional EBNA-1.

In yet a further particular embodiment, the expression system comprises: (a) a first vector comprising the first genetic entity, the third genetic entity, and the fourth genetic entity; and (b) a second vector comprising the second genetic entity. Particularly, the second vector does not encompass a functional Epstein Barr virus OriP sequence and does not encompass a nucleic acid sequence encoding a functional EBNA-1.

In yet a further particular embodiment, the expression system comprises: (a) a first vector comprising the second genetic entity, the third genetic entity, and the fourth genetic entity; and (b) a second vector comprising the first genetic entity. Particularly, the first vector does not encompass a nucleic acid sequence encoding a functional EBNA-1, and the second vector does not encompass a functional Epstein Barr virus OriP sequence.

The vector(s) to be employed in connection with the present invention is (are) (an) expression vector(s), that is, a self-replicating genetic construct including at least one "expression cassette" (in which any one or more of the first genetic entity the second genetic entity, the third genetic entity, and the fourth genetic entity may be inserted). The term "expression cassette", as used herein, refers to a genetic construct that is capable of expressing a nucleic acid sequence (i.e. a "heterologous" nucleic acid sequence). This requires that such expression cassette comprises regulatory sequence elements which contain information regarding to transcriptional and/or translational regulation, and that such regulatory sequences are "operably linked" to the nucleic acid sequence of interest. An operable linkage is a linkage in which the regulatory sequence elements and the nucleic acid sequence to be expressed are connected in a way that enables gene expression. An expression vector may comprise a single expression cassette or a plurality of two or more expression cassettes, optionally further comprising regulatory sequences enabling coordinated expression of the respective nucleic acid sequences of interest.

The precise nature of the regulatory sequence elements of an "expression cassette" that are necessary for controlling and driving gene expression may vary among species, but in general these regions comprise promoter regulatory sequences (i.e. a sequence region located 5' ("upstream") of the nucleic acid sequence of interest) and 3'-untranslated regulatory sequences (i.e. a sequence region located 3' ("downstream") of the nucleic acid sequence of interest).

The term "promoter", used herein, denotes sequence elements that per se direct the initiation of transcription (e.g., binding sites for transcription factors and for DNA-dependent RNA-polymerase, TATA box, CAAT sequences, and 5'-capping elements). As long as this functionality of promoting transcription initiation is retained or substantially retained (e.g., at least 70%, at least 80%, at least 90% or at least 95% of wild-type activity, that is, activity of a full-length sequence), any truncated, mutated or otherwise modified variants of a (naturally occurring) wild-type promoter sequence are also within the above definition. As used herein, the term "core promoter" refers to a sequence of minimal length that retains promoter activity. As used herein, the promoter sequence is operably linked to the transcriptional start site of the nucleic acid sequence to be expressed. Suitable promoters include inter alia SV40 early and late promoters, RSV and CMV promoters, and yeast A0X1 and GAL1 promoters.

In particular embodiments, the expression cassettes used herein comprise a promoter sequence from murine cytomegalovirus (mCMV), preferably promoter sequences of the mCMV immediate early (IE) genes, such as mCMV IE1 and mCMV 1E2 (Dorsch-Hasler, K. et al. (1985) *Proc. Natl. Acad. Sci. USA* 82, 8325-8329; Messerle, M. et al. (1991) *J. Virol.* 65, 1638-1643). In other particular embodiments, the expression vectors of the present invention comprise (as part of an expression cassette) a promoter sequence from human cytomegalovirus (hCMV), preferably, promoter sequences of the hCMV immediate early (IE) genes, such as hCMV IE1 and hCMV IE2 (You, C. Y. et al. (1992) *Intervirology* 34, 94-104; Klucher, K. M. et al. (1993) *Mol. Cell. Biol.* 13, 1238-1250), are employed, with the hCMV IE1 promoter being particularly preferred.

Furthermore, the promoter regulatory sequences of an expression cassette, as defined herein, may comprise an "enhancer" sequence. The term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a (naturally occurring) wild-type enhancer sequence are also within the above definition.

In particular embodiments, any hCMV and/or simian cytomegalovirus (sCMV) sequences can be employed as enhancer sequence. Preferably, sequences of the hCMV and/or sCMV immediate early (IE) genes, such as hCMV IE1, hCMV IE2, sCMV IE1, and sCMV IE2 (Meier, J. L. and Stinski, M. F. (1996) *Intervirology* 39, 331-342; Kim, G. Y. et al. (2011) *Biotechnol. Lett.* 33, 1319-1326), are employed, with the hCMV and/or sCMV IE1 enhancer sequences being particularly preferred.

In further particular embodiments, the expression cassettes, as used herein, comprise chimeric promoter regulatory sequences that are composed of a promoter sequence from the murine or human cytomegalovirus IE1 promoter and an enhancer sequence from the human and/or simian cytomegalovirus IE1 region provided that sequences from two different cytomegalovirus species are encompassed. Such chimeric promoters are disclosed in international patent application PCT/EP2013/069715 (published as WO 2014/044845).

In addition, the 3' non-coding regulatory sequences may contain regulatory elements involved in transcriptional termination, polyadenylation, or the like. If, however, these termination sequences are not satisfactorily functional in a particular mammalian host cell, then they may be substituted with signals functional in that cell. The skilled person is well aware of all these regulatory elements, and the selection of such elements suitable for the expression of a nucleic acid molecule in a given setting is within his common knowledge.

(i) The first genetic entity of the expression system according to the present invention comprises a nucleic acid sequence encoding a functional Epstein Barr virus nuclear antigen 1 (EBNA-1), the nucleic acid sequence being operably linked to (preferably 5' and 3') regulatory elements that allow for expression of the nucleic acid sequence encoding a functional EBNA-1.

The Epstein Barr virus nuclear antigen 1 (EBNA-1) is a nuclear phosphoprotein that binds with high affinity to three major DNA binding sites within the Epstein Barr virus (EBV) genome (Rawlins, D. R. et al. (1985) *Cell* 42, 859-868; Kennedy, G., and Sugden, B. (2003) *Mol. Cell. Biol.* 23 6901-6908). One such DNA binding region resides in the OriP sequence of EBV. Binding of EBNA-1 (via its C-terminal DNA binding region) to OriP is essential for plasmid DNA replication and episome maintenance (Altmann, M. et al. (2006) *Proc. Natl. Acad. Sci. USA* 103, 14188-14193). The nucleotide sequence of EBNA-1 is well established in the art (Yates, J. L. et al. (1984) *Proc. Natl. Acad. Sci. USA* 81, 3806-3810) and can also be derived from the EBV genome sequence (GenBank accession no. V01555.2).

The term "encoding a functional EBNA-1", as used herein, is to be understood in that any EBNA-1 nucleic acid sequence may be encoded as long as the functionality of the EBNA-1 protein (in particular, its DNA-binding capacity) is not significantly reduced, for example, is at least 80% of the activity of the full-length protein, or at least 85% of the activity of the full-length protein, or at least 90% of the activity of the full-length protein, or at least 95% of the activity of the full-length protein. The skilled person is well aware of assays for determining the functionality of EBNA-1, for example for measuring DNA-binding activity.

In specific embodiments, the functional variants of the EBNA-1 wild-type protein encoded by the nucleic acid sequence of the first genetic entity exhibit over their total lengths an amino acid identity of at least 80%, or of at least 85%, or of at least 90%, or of at least 95% with the EBNA-1 wild-type protein.

In a preferred embodiment, the nucleic acid sequence encoding a functional EBNA-1 is selected from the group of sequences consisting of SEQ ID NO: 1 and SEQ ID NO: 2. Depending on the mammalian host cell employed, the nucleic acid sequences given below may vary due to differences in codon usage.

SEQ ID NO: 1 (1926 nucleotides in length) represents the full-length EBNA-1 sequence.

```
  1 atgtctgacg aggggccagg tacaggacct ggaaatggcc taggagagaa 51 gggagacaca tctggaccag aaggctccgg cggcagtgga cctcaaagaa 101 gagggggtga taaccatgga cgaggacggg gaagaggacg aggacgagga 151 ggcggaagac caggagcccc gggcggctca ggatcagggc caagacatag 201 agatggtgtc cggagacccc aaaaacgtcc aagttgcatt ggctgcaaag 251 ggacccacgg tggaacagga gcaggagcag gagcgggagg ggcaggagca 301 ggaggggcag gagcaggagg aggggcagga gcaggaggag gggcaggagg 351 ggcaggaggg gcaggagggg caggagcagg aggaggggca ggagcaggag 401 gaggggcagg aggggcagga ggggcaggag caggaggagg ggcaggagca 451 ggaggagggg caggaggggc aggagcagga ggaggggcag gaggggcagg 501 aggggcagga gcaggaggag gggcaggaga aggaggaggg gcaggagggg 551 caggagcagg aggaggggca ggaggggcag gaggggcagg agcaggagga 601 ggggcaggag caggaggggc aggaggggca ggaggggcag gagcaggagg 651 ggcaggagca ggaggagggg caggaggggc aggaggggca ggagcaggag
```

```
 701 gggcaggagc aggaggggca ggagcaggag gggcaggagc aggaggggca 751 ggaggggcag gagcaggagg ggcaggaggg gcaggagcag gaggggcagg 801 aggggcagga gcaggaggag gggcaggagg ggcaggagca ggaggagggg 851 caggaggggc aggagcagga ggggcaggag gggcaggagc aggaggggca 901 ggaggggcag gagcaggagg ggcaggaggg gcaggagcag gaggagtgggc 951 aggagcagga ggggcaggag caggaggtgg aggccggggt cgaggaggca 1001 gtggaggccg gggtcgagga ggtagtggag gccggggtcg aggaggtagt 1051 ggaggccgcc ggggtagagg acgtgaaaga gccagggggg gaagtcgtga 1101 aagagccagg gggagaggtc gtggacgtgg agaaaagagg cccaggagtc 1151 ccagtagtca gtcatcatca tccgggtctc caccgcgcag gcccctcca 1201 ggtagaaggc cattttttcca ccctgtaggg gaagccgatt attttgaata 1251 ccaccaagaa ggtggcccag atggtgagcc tgacgtgccc ccgggagcga 1301 tagagcaggg ccccgcagat gacccaggag aaggcccaag cactggaccc 1351 cggggtcagg gtgatggagg caggcgcaaa aaaggagggt ggtttggaaa 1401 gcatcgtggt caaggaggtt ccaacccgaa atttgagaac attgcagaag 1451 gtttaagagc tctcctggct aggagtcacg tagaaaggac taccgacgaa 1501 ggaacttggg tcgccggtgt gttcgtatat ggaggtagta agacctccct 1551 ttacaaccta aggcgaggaa ctgcccttgc tattccacaa tgtcgtctta 1601 caccattgag tcgtctcccc tttggaatgg cccctggacc cggcccacaa 1651 cctggcccgc taagggagtc cattgtctgt tatttcatgg tctttttaca 1701 aactcatata tttgctgagg ttttgaagga tgcgattaag gaccttgtta 1751 tgacaaagcc cgctcctacc tgcaatatca gggtgactgt gtgcagcttt 1801 gacgatggga tagatttgcc tccctggttt ccacctatgg tggaagggc 1851 tgccgcggag ggtgatgacg gagatgacgg agatgaagga ggtgatggag 1901 atgagggtga ggaagggcag gagtga
```

The nucleic acid sequence of SEQ ID NO: 1 encodes the EBNA-1 polypeptide having the amino acid sequence of SEQ ID NO: 7 (641 amino acids in length).

```
  1 MSDEG PGTGP GNGLG EKGDT SGPEG SGGSG PQRRG GDNHG

41 RGRGR GRGRG GGRPG APGGS GSGPR HRDGV RRPQK RPSCI

81 GCKGT HGGTG AGAGA GGAGA GGAGA GGGAG AGGGA GGAGG

121 AGGAG AGGGA GAGGG AGGAG GAGAG GGAGA GGGAG GAGAG

161 GGAGG AGGAG AGGGA GAGGG AGGAG AGGGA GGAGG AGAGG

201 GAGAG GAGGA GGAGA GGAGA GGGAG GAGGA GAGGA GAGGA

241 GAGGA GAGGA GGAGA GGAGG AGAGG AGGAG AGGGA GGAGA

281 GGGAG GAGAG GAGGA GAGGA GGAGA GGAGG AGAGG GAGAG

321 GAGAG GGGRG RGGSG GRGRG GSGGR GRGGS GGRRG RGRER

361 ARGGS RERAR GRGRG RGEKR PRSPS SQSSS SGSPP RRPPP

401 GRRPF FHPVG EADYF EYHQE GGPDG EPDVP PGAIE QGPAD

441 DPGEG PSTGP RGQGD GGRRK KGGWF GKHRG QGGSN PKFEN

481 IAEGL RALLA RSHVE RTTDE GTWVA GVFVY GGSKT SLYNL

521 RRGTA LAIPQ CRLTP LSRLP FGMAP GPGPQ PGPLR ESIVC

561 YFMVF LQTHI FAEVL KDAIK DLVMT KPAPT CNIRV TVCSF

601 DDGVD LPPWF PPMVE GAAAE GDDGD DGDEG GDGDE GEEGQ

641 E
```

SEQ ID NO: 2 (1254 nucleotides in length) represents a truncated EBNA-1 nucleic acid sequence.

```
  1 atgtctgacg aggggccagg tacaggacct ggaaatggcc taggagagaa 51 gggagacaca tctgaccag aaggctccgg cggcagtgga cctcaaagaa 101 gagggggtga taaccatgga cgaggacggg gaagaggacg aggacgagga
```

```
     151  ggcggaagac  caggagcccc  gggcggctca  ggatcagggc  caagacatag 201  agatggtgtc  cggagacccc  aaaaacgtcc  aagttgcatt  ggctgcaaag 251  ggacccacgg  tggaacagga  gcaggagcag  gagcgggagg  ggcaggagca 301  ggaggtggag  gccggggtcg  aggaggcagt  ggaggccggg  gtcgaggagg 351  tagtggaggc  cggggtcgag  gaggtagtgg  aggccgccgg  ggtagaggac 401  gtgaaagagc  caggggggga  agtcgtgaaa  gagccagggg  gagaggtcgt 451  ggacgtggag  aaaagaggcc  caggagtccc  agtagtcagt  catcatcatc 501  cgggtctcca  ccgcgcaggc  cccctccagg  tagaaggcca  tttttccacc 551  ctgtagggga  agccgattat  tttgaatacc  accaagaagg  tggcccagat 601  ggtgagcctg  acgtgccccc  gggagcgata  gagcagggcc  ccgcagatga 651  cccaggagaa  ggcccaagca  ctggaccccg  gggtcagggt  gatggaggca 701  ggcgcaaaaa  aggagggtgg  tttggaaagc  atcgtggtca  aggaggttcc 751  aacccgaaat  ttgagaacat  tgcagaaggt  ttaagagctc  tcctggctag 801  gagtcacgta  gaaaggacta  ccgacgaagg  aacttgggtc  gccggtgtgt 851  tcgtatatgg  aggtagtaag  acctcccttt  acaacctaag  gcgaggaact 901  gcccttgcta  ttccacaatg  tcgtcttaca  ccattgagtc  gtctcccctt 951  tggaatggcc  cctggacccg  gcccacaacc  tggcccgcta  agggagtcca 1001  ttgtctgtta  tttcatggtc  ttttacaaa   ctcatatatt  tgctgaggtt 1051  ttgaaggatg  cgattaagga  ccttgttatg  acaaagcccg  ctcctacctg 1101  caatatcagg  gtgactgtgt  gcagctttga  cgatggagta  gatttgcctc 1151  cctggtttcc  acctatggtg  gaaggggctg  ccgcggaggg  tgatgacgga 1201  gatgacggag  atgaaggagg  tgatggagat  gagggtgagg  aagggcagga 1251  gtga
```

The nucleic acid sequence of SEQ ID NO: 2 encodes the EBNA-1 polypeptide having the amino acid sequence of SEQ ID NO: 8 (417 amino acids in length).

```
  1 MSDEG PGTGP GNGLG EKGDT SGPEG SGGSG PQRRG GDNHG

41 RGRGR GRGRG GGRPG APGGS GSGPR HRDGV RRPQK RPSCI

81 GCKGT HGGTG AGAGA GGAGA GGGGR GRGGS GGRGR GGSGG

121 RGRGG SGGRR GRGRE RARGG SRERA RGRGR GRGEK RPRSP

161 SSQSS SSGSP PRRPP PGRRP FFHPV GEADY FEYHQ EGGPD

201 GEPDV PPGAI EQGPA DDPGE GPSTG PRGQG DGGRR KKGGW

241 FGKHR GQGGS NPKFE NIAEG LRALL ARSHV ERTTD EGTWV

281 AGVFV YGGSK TSLYN LRRGT ALAIP QCRLT PLSRL PFGMA

321 PGPGP QPGPL RESIV CYFMV FLQTH IFAEV LKDAI KDLVM

361 TKPAP TCNIR VTVCS FDDGV DLPPW FPPMV EGAAA EGDDG

401 DDGDE GGDGD EGEEG QE
```

The nucleic acid sequence encoding a functional Epstein Barr virus nuclear antigen 1 (EBNA-1) is operably linked to (preferably 5' and 3') regulatory elements as defined herein above.

(ii) The second genetic entity of the expression system according to the invention comprises a nucleic acid sequence encoding a functional nucleoside diphosphate kinase A (NDPK-A), the nucleic acid sequence being operably linked to (preferably 5' and 3') regulatory elements that allow for expression of the nucleic acid sequence encoding a functional NDPK-A.

Nucleoside diphosphate kinase A (NDPK-A) represents a nuclear shuttle protein that facilitates channeling of nucleoside triphosphates into protein synthesis and DNA replication complexes (Ray, N. B., and Mathews, C. K. (1992) *Curr. Top. Cell. Regul.* 33, 343-357; Gerbitz, K. D. et al. (1996) *Diabetes* 45, 113-126). The nucleotide sequence of NDPK-A is known from various mammalian species including human, mouse, and hamster and can be derived from GenBank or other established databases.

The term "encoding a functional NDPK-A", as used herein, is to be understood in that any NDPK-A nucleic acid sequence may be encoded as long as the functionality of the NDPK-A protein is not significantly reduced, for example, is at least 80% of the activity of the full-length protein, or at least 85% of the activity of the full-length protein, or at least 90% of the activity of the full-length protein, or at least 95% of the activity of the full-length protein. The skilled person is well aware of assays for determining the functionality NDPK-A.

In specific embodiments, the functional variants of the NDPK-A wild-type protein encoded by the nucleic acid sequence of the second genetic entity exhibit over their total lengths an amino acid identity of at least 80%, or of at least 85%, or of at least 90%, or of at least 95% of the NDPK-A wild-type protein. For example, the NDPK-A nucleic acid sequences of different mammalian species may be employed. In a preferred embodiment, the hamster NDPK-A nucleic acid sequence is used. Depending on the mammalian host cell employed, the nucleic acid sequences given below may vary due to differences in codon usage.

In a preferred embodiment, the nucleic acid sequence encoding NDPK-A has the sequence of SEQ ID NO: 3 (459 nucleotides in length represents the cDNA from Chinese hamster).

```
  1 atggccaaca gtgagcgcac cttcattgct atcaagcctg atggggtcca 51 gcggggtctg gtgggcgaga tcatcaagcg ttttgaacag aagggattcc 101 gacttgttgg cctgaaattt atgcaggctt cagaggacct tctcaaagag 151 cactacattg acctgaagga ccgtcccttc tttactggcc tagtgaaata 201 catgcattca ggaccagtgg ttgctatggt ctgggagggg ttgaatgttg 251 tgaagacagg ccgggtgatg cttggagaga ccaaccctgc agactctaaa 301 cctgggacca ttcgaggaga cttttgcatc caagttggca ggaacatcat 351 tcatggcagc gattctgtgg agagtgcaga gaaggagatc ggcttgtggt 401 ttcagcctga ggagctggtg gattacaaga gctgtgcaca aaactggatc 451 tatgagtga
```

The nucleic acid sequence of SEQ ID NO: 3 encodes the NDPK-A polypeptide having the amino acid sequence of SEQ ID NO: 9 (152 amino acids in length).

```
  1 MANSE RTFIA IKPDG VQRGL VGEII KRFEQ KGFRL VGLKF

41 MQASE DLLKE HYIDL KDRPF FTGLV KYMHS GPVVA MVWEG

81 LNVVK TGRVM LGETN PADSK PGTIR GDFCI QVGRN IIHGS

121 DSVES AEKEI GLWFQ PEELV DYKSC AQNWI YE
```

The nucleic acid sequence encoding a functional nucleoside diphosphate kinase A (NDPK-A) is operably linked to (preferably 5' and 3') regulatory elements as defined herein above.

(iii) The third genetic entity of the expression system according to the present invention comprises the nucleic acid sequence of interest being operably linked to (preferably 5' and 3') regulatory elements that allow for expression of the nucleic acid sequence of interest.

The nucleic acid sequence to be expressed may encode any polypeptides or proteins of interest, in particular polypeptides or proteins having diagnostic or therapeutic applicability, such as inter alia growth factors, cytokines (e.g., interferons, interleukins), hormones, tyrosine kinases, receptors (e.g., GPCRs), integrins, transcription factors, blood clotting factors, antibodies, antibody fragments, anticalins, and the like.

The expression system as defined herein may be employed for the expression of a single nucleic acid sequence of interest encoding a single polypeptide or protein or a plurality of two or more nucleic acid sequences of interest encoding different polypeptides or proteins. In specific embodiments, the different polypeptides represent subunits of a dimeric or multimeric protein, such as inter alia homomeric or heteromeric receptor molecules, peptide hormones, DNA/RNA polymerases, hemoglobins, vaccines, and the like.

In particularly preferred embodiments, the nucleic acid sequence of interest encodes an antibody or an antibody fragment (such as inter alia Fab fragments, F(ab)$_2$ fragments, F(ab') fragments, F(ab')$_2$ fragments, single-chain Fvs). For example, a first nucleic acid sequence of interest may encode the antibody light chain, and a second nucleic acid sequence of interest may encode the antibody heavy chain. The antibody molecule may be a naturally occurring or a genetically engineered antibody, either a full-length antibody or a truncated variant thereof (such as Fab fragments, F(ab)$_2$ fragments, F(ab') fragments, F(ab')$_2$ fragments, single-chain Fvs). IgG immunoglobulin antibodies are particularly preferred. Depending on the specific application, the antibody molecules may be chimeric (e.g., murine/human), humanized or fully human.

The nucleic acid sequence of interest to be expressed is operably linked to (preferably 5' and 3') regulatory elements as defined herein above.

(iv) The fourth genetic entity of the expression system according to the present invention comprises the Epstein Barr virus OriP sequence or one or more subsequences thereof, wherein the one or more subsequences comprise at least the 'Family of Repeats' DNA-binding site for EBNA-1 and the 'Dyad Symmetry' DNA-binding site for EBNA-1.

The OriP region of EBV has a total length of about 1800 nucleotides and comprises two non-contiguous regions that are required for activity with a distance of about 1000 nucleotides in-between. One consists of 20 copies of an imperfect 30 nucleotide-repeat sequence, which is referred to as 'Family of Repeats'. The other region referred to as 'Dyad Symmetry' is 140 nucleotides in length and contains a 65-nucleotide region of dyad symmetry. Both elements are DNA-binding sites for EBNA-1 (Hudson, G. S. et al. (1985) supra; Reisman, D. et al. (1985) supra). The OriP sequence can also be derived from the EBV genome sequence (GenBank accession no. V01555.2).

The second genetic entity of the expression system may comprise the entire OriP sequence of EBV or any truncations or subsequences thereof provided that the truncations or subsequences comprise at least the 'Family of Repeats' DNA-binding site for EBNA-1 and the 'Dyad Symmetry' DNA-binding site for EBNA-1.

In a preferred embodiment, the nucleic acid sequence encoding the 'Family of Repeats' DNA-binding site for EBNA-1 has the sequence of SEQ ID NO: 5 and the nucleic acid sequence encoding the 'Dyad Symmetry' DNA-binding site for EBNA-1 has the sequence of SEQ ID NO: 6.

SEQ ID NO: 4 encompasses the EBV OriP 'Family of Repeats' region and has a length of 494 nucleotides.

```
  1 ggatagcata tgctacccag atatagatta ggatagccta tgctacccag
 51 atataaatta ggatagcata tactacccag atatagatta ggatagcata
101 tgctacccag atatagatta ggatagccta tgctacccag atatagatta
151 ggatagcata tgctacccag atatagatta ggatagcata tgcaatccag
201 atatttgggt agtatatgct acccagatat aaattaggat agcatatact
251 accctaatct ctattaggat agcatatgct acccggatac agattaggat
301 agcatatact acccagatat agattaggat agcatatgct acccagatat
351 agattaggat agcctatgct acccagatat aaattaggat agcatatact
401 acccagatat agattaggat agcatatgct acccagatat agattaggat
451 agcctatgct acccagatat agattaggat agcatatgct atcc
```

SEQ ID NO: 5 encompasses the EBV OriP 'Dyad Symmetry' region and has a length of 140 nucleotides.

```
  1 atcgctgttc cttaggaccc ttttactaac cctaattcga tagcatatgc
 51 ttcccgttgg gtaacatatg ctattgaatt agggttagtc tggatagtat
101 atactactac ccgggaagca tatgctaccc gtttaggggtt
```

In particular embodiments, the expression system according to the present invention further comprises a nucleic acid sequence encoding one or more DNA-binding sites for EBNA-1, wherein the one or more DNA-binding sites are not encompassed in the Epstein Barr virus OriP sequence.

These DNA-binding sites for EBNA-1 may be any binding sequences having specific affinity for EBNA-1. Particularly, these DNA-binding sites for EBNA-1 are human chromosomal sequences such as the Chr11.1 binding site in the chromosome 11 cluster as well as Motif 2, Motif 3, Motif 4, and Motif 5, all described in Lu, F. et al. (2010) *Virology Journal* 7, 262. The binding sites Chr11.1 and Motif 2 are preferred, as they bind directly to EBNA-1 without the requirement for mediation. The nucleic acid sequence of may comprise a single type of DNA-binding site for EBNA-1 (e.g., Motif 2) or two or more DNA-binding sites for EBNA-1 (e.g., Motif 2 and Chr11.1). The one or more DNA-binding sites may be present as single copy or in two or more copies, for example arranged as tandem repeats.

The nucleic acid sequence encoding the one or more DNA-binding sites for EBNA-1 may have the sequence of SEQ ID NO: 6 (90 nucleotides in length), comprising two copies of the Chr11.1 binding site (underlined) and two copies of the Motif 2 binding site (bold and in italics).

as between bacterial and fungal cells or between bacteria and animal cells. Suitable origins of replication for prokaryotic cells include, for example, the ColE1 and M13 origins of replications.

In another preferred embodiment, the expression system comprises at least one nucleic acid sequence encoding a selection marker (typically in operable linkage to 5' and 3' regulatory elements as described herein above). The term "selection marker", as used herein, denotes a nucleic acid sequence that allows cells carrying the same to be specifically selected for or against, in the presence of a corresponding selection agent.

A useful positive resistance gene is an antibiotic resistance gene. This selection marker allows the host cell transformed with the gene to be positively selected for in the presence of the corresponding antibiotic; a non-transformed host cell would not be capable to grow or survive under the selective culture conditions. Selection markers can be positive, negative or bifunctional. Positive selection markers allow selection for cells carrying the marker, whereas negative selection markers allow cells carrying the marker to be selectively eliminated. Typically, a selection marker will confer resistance to a drug or compensate for a metabolic or catabolic defect in the host cell. Suitable resistance genes for mammalian cells include inter alia the genes coding for hygromycin phosphotransferase, neomycin phosphotransferase, dihydrofolate reductase, thymidine kinase, glutamine synthetase, asparagine synthetase, tryptophan synthetase, histidinol dehydrogenase, and genes encoding resistance to

```
  1 tggataataa gtgttgcctc gt gggtaacc gggcagcatg ctacctggat
 51 aataagtgtt gcctcgtggg taaccgggca gcatgctacc
```

For the purpose of independent replication, the expression vectors employed herein comprise an origin of replication that is functional in mammalian cells, such as the SV40 origin of replication. Specifically designed expression vectors (i.e. shuttle vectors) comprise more than one origin of replication allow the shuttling between different hosts, such puromycin, bleomycin, phleomycin, chloramphenicol, zeocin, and mycophenolic acid. In a particularly preferred embodiment, the nucleic acid sequence encoding a selection marker encodes glutamine synthase (Cockett, D. K. et al. (1990) *Bio/Technology* 8, 662-667; Bebbington, C. R. et al. (1992) *Bio/Technology* 10:169-175).

Apart from selection in the presence of a corresponding selection agent a selection marker to be employed can also provide a nucleic acid sequence encoding a molecule normally not present in the cell, e.g. green fluorescent protein (GFP) or enhanced GFP (eGFP). Cells harboring such nucleic acid sequence encoding GFP or eGFP can easily be distinguished from cells not harboring this gene, only by the detection of the fluorescence emitted.

The expression system according to the present invention may comprise a single selection marker or a plurality of two or more selection markers. For example, if the expression system comprises a first vector and a second vector, then either vector may comprise a suitable selection marker. The respective selection markers encompassed in the first vector and the second vector may be identical (e.g., glutamine synthase) or may be different (e.g., glutamine synthase and enhanced green fluorescent protein). It is also possible that a single vector comprises two or more selection markers.

In specific embodiments, the expression system is further characterized by any one or more of the following structural features:
(a) the nucleic acid sequence encoding a functional EBNA-1 is selected from the group of sequences consisting of SEQ ID NO: 1 and SEQ ID NO: 2;
(b) the nucleic acid sequence encoding a functional NDPK-A has the sequence of SEQ ID NO: 3;
(c) the nucleic acid sequence encoding the 'Family of Repeats' DNA-binding site for EBNA-1 has the sequence of SEQ ID NO: 4 and the nucleic acid sequence encoding the 'Dyad Symmetry' DNA-binding site for EBNA-1 has the sequence of SEQ ID NO: 5; and
(d) the expression system further comprises at least one nucleic acid sequence encoding a selection marker, the selection marker particularly being glutamine synthase.

In a preferred embodiment, the expression system of the present invention comprises:
(a) a first expression vector, comprising:
    (ia) an EBNA-1 encoding nucleic acid sequence selected from the group consisting of SEQ ID NO: 1 and SEQ ID NO: 2; and
    (iia) a NDPK-A encoding nucleic acid sequence of SEQ ID NO: 3; wherein the first expression vector does not encompass a functional Epstein Barr virus OriP sequence; and
(b) a second expression vector, comprising:
    (ib) a nucleic acid sequence of interest; and
    (iib) a nucleic acid sequence encoding the 'Family of Repeats' DNA-binding site of SEQ ID NO: 4 and a nucleic acid sequence encoding the 'Dyad Symmetry' DNA-binding site of SEQ ID NO: 5
    wherein the second genetic entity does not encompass a nucleic acid sequence encoding a functional EBNA-1.

In another preferred embodiment, the expression system of the present invention comprises:
(a) a first expression vector, comprising:
    (ia) an EBNA-1 encoding nucleic acid sequence selected from the group consisting of SEQ ID NO: 1 and SEQ ID NO: 2;
    (iia) a NDPK-A encoding nucleic acid sequence of SEQ ID NO: 3; and
    (iiia) a nucleic acid sequence encoding glutamine synthase as selection marker; wherein the first genetic entity does not encompass a functional Epstein Barr virus OriP sequence; and
(b) a second expression vector, comprising:
    (ib) a nucleic acid sequence of interest;
    (iib) a nucleic acid sequence encoding the 'Family of Repeats' DNA-binding site of SEQ ID NO: 5 and a nucleic acid sequence encoding the 'Dyad Symmetry' DNA-binding site of SEQ ID NO: 6; and
    (iiib) a nucleic acid sequence encoding enhanced green fluorescent protein as selection marker,
    wherein the second genetic entity does not encompass a nucleic acid sequence encoding a functional EBNA-1.

An ample number of expression vectors and other cloning vehicles have been established in the art and commercially available from numerous suppliers. The skilled person is well aware how as to select a suitable vector for a particular application (see also, e.g., Sambrook, J., and Russel, D. W. (2001) supra; and Ausubel, F. M. et al. (2001) supra).

In a further preferred embodiment, the expression system allows for the transient expression of the nucleic acid sequence of interest in a mammalian cell. The term "transient expression", as used herein, refers to a process of introducing and expressing genetic material into a host cell, wherein the introduced (i.e. transfected) genetic material is only transiently present in the host cell. Since the genetic material introduced is not integrated into the nuclear genome and maintained as extra-chromosomal element (e.g., an episome), it will be diluted from one generation to the next or degraded. Introduction of the genetic material into the host cell is accomplished by means of cell transfection (cf. below).

In a particular embodiment of such transient expression system, all four of the first genetic entity, the second genetic entity, the third genetic entity, and the fourth genetic entity are transiently introduced into the host cell and are capable of independent replication (e.g., as an episome). In another particular embodiment, only any one, any two or any three of the first genetic, entity the second genetic entity, the third genetic entity, and the fourth genetic entity is/are transiently introduced into the host cell and are capable of independent replication, whereas the respective remaining one, two or three genetic entity (entities) become(s) stably integrated in the host cell genome due to the presence of an appropriate selection marker.

In a further specific embodiment, the expression system allows for the stable expression of the nucleic acid sequence of interest in a mammalian cell. In a particular embodiment of such stable expression system, all four of the first genetic entity, the second genetic entity, the third genetic entity, and the fourth genetic entity are introduced into the host cell and stably integrated into the host cell genome by utilizing appropriate selection markers.

In a further aspect, the present invention relates to a mammalian host cell comprising the expression system as defined herein above. Within the present invention, virtually any mammalian cell can be employed as host cell including inter alia cells derived from mouse, rat, hamster, rabbit, cat, dog, pig, cow, horse, monkey, and human. In a specific embodiment, the host cell is of human origin. In another specific embodiment, the host cell is derived from hamster, particularly from Chinese hamster.

Suitable mammalian cells include inter alia immortalized cell lines such as human Hela, HEK293, H9, MCF7, and Jurkat cells, mouse NIH3T3, C127, and L cells, simian COS1 and COS7 cells, quail QC1-3 cells, and CHO cells. All these host cells may be obtained from depositories such as the American Type Culture Collection (Manassas, Va., USA) or the Deutsche Sammlung von Mikroorganismen and Zellkulturen (Braunschweig, Germany) as well as from various commercial suppliers. Also within the present invention are primary mammalian cells, that is, cells directly obtained from an organism (at any developmental stage including inter alia blastocytes, embryos, larval stages, and adults). Examples of suitable primary cells comprise cardiomyocytes, primary hepatocytes, fibroblasts, neuronal cells, as well as stem cells. Also within the present invention are immortalized stable cell lines derived from primary cells.

In a preferred embodiment, the mammalian host cell is a Chinese hamster ovary (CHO) cell. Suitable CHO cell lines include inter alia CHO KI (Tjio, J. T. and Puck, T. T. (1958) *J. Exp. Med.* 108, 945-955), CHO pro3-, CHO DG44, CHO P12, dhfr-negative DUK-B11 (Urlaub, G. and Chasin L. A. (1980) *Proc. Natl. Acad. Sci. USA* 77, 4216-4220), CHO 9B, and particularly CHOK1SV (Lonza Ltd. Basel, Switzerland). CHOK1SV is a suspension, protein-free adapted CHOK1 derivative utilizing the glutamine synthetase (GS) gene expression system: positive transfectants were obtained under dual selection of methionine sulfoximine and glutamine-free media. In a particularly preferred embodiment, the host cell is a CHO cell lacking glutamine synthase, such as CHOK1SV GS cells ("CHO Xceed"), Lonza Ltd., Basel, Switzerland).

The skilled person is well aware how as to select appropriate host cells for a particular application. Standard cell culture techniques for mammalian cells are well established in the art and described, e.g., Bonifacino, J. S. et al. (2002) *Current Protocols in Cell Biology*, Wiley & Sons, Hoboken, N.J.

In another aspect, the present invention relates to a method for the production of the mammalian host cell as defined herein, comprising:
(i) providing a mammalian cell;
(ii) transfecting the mammalian cell with the first genetic entity, the second genetic entity, the third genetic entity, and the fourth genetic entity as defined herein.

In a particular embodiment, the present invention relates to a method for the production of the mammalian host cell as defined herein, comprising:
(i) providing a mammalian cell;
(ii) transfecting the mammalian cell with any one or more of the first genetic entity, the second genetic entity, the third genetic entity, and the fourth genetic entity as defined herein; and
(iii) transfecting the cell obtained in (ii) with the remaining any one or more of the first genetic entity, the second genetic entity, the third genetic entity, and the fourth genetic entity as defined herein.

In one embodiment, the method is performed as in vitro or ex vivo method.

The term "transfecting", as used herein, denotes the introduction of (heterologous) genetic material into the mammalian host cell. Transfection may be transient, as defined herein above (resulting in transient expression of the genetic material). Alternatively, transfection may be stable, as defined herein above (resulting in stable expression of the genetic material by integration in the host cell genome). Numerous methods for transfecting mammalian cells are well established in the art (see, e.g., Sambrook, J., and Russel, D. W. (2001) supra; and Ausubel, F. M. et al. (2001) supra), including chemical transfection methods (e.g., using calcium phosphate, dendrimers, liposomes, lipofectamine, or cationic polymers, such as DEAE-dextran and polyethyleneimine) as well as non-chemical transfection methods (e.g., by electroporation, cell squeezing, sonoporation, impalefection, magnetofection, and using a gene gun).

The term "any one or more", as used herein, denotes any one, any two, any three or all four of the first genetic entity, the second genetic entity, the third genetic entity, and the fourth genetic entity as defined herein. Transfection of any two or more of the first genetic entity, the second genetic entity, the third genetic entity, and the fourth genetic entity as defined herein may be performed concomitantly or in any order.

In a specific embodiment of the method, step (ii) further comprises: selecting a mammalian cell stably transfected with the any one or more of the first genetic entity, the second genetic entity, the third genetic entity, and the fourth genetic entity as defined herein. This may be accomplished by means of one or more appropriate selection markers (e.g., expression of glutamine synthetase (GS) gene in a GS-deficient host cell).

In a further aspect, the present invention relates to a kit-of-parts for the production of the mammalian host cell as defined herein, comprising: (i) a mammalian cell; and (ii) the first genetic entity, the second genetic entity, the third genetic entity, and the fourth genetic entity as defined herein as defined herein above.

In a preferred embodiment, the mammalian host cell is a Chinese hamster ovary (CHO) cell, and particularly preferably a CHO cell lacking glutamine synthase (cf. above). In another preferred embodiment, the first genetic entity, the second genetic entity, the third genetic entity, and the fourth genetic entity are comprised in one or more vectors.

The kit-of-parts may further comprise any one or more of: culture media and supplements, transfection reagents, selection agents, detection reagents for determining transfection efficacies, and instructions of use.

In a further aspect, the present invention relates to a method for the expression of a nucleic acid sequence of interest in a mammalian cell, comprising:
(i) transfecting a mammalian cell with the first genetic entity, the second genetic entity, the third genetic entity, and the fourth genetic entity as defined herein;
(iii) culturing the mammalian cell obtained in (i) under conditions allowing for the expression of the nucleic acid sequence of interest.

Transfection may be transient or stable or a combination thereof (cf. the definitions above).

In a particular embodiment, the present invention relates to a method for the expression of a nucleic acid sequence of interest in a mammalian cell, comprising:
(i) transfecting a mammalian cell with any one or more of the first genetic entity, the second genetic entity, the third genetic entity, and the fourth genetic entity as defined herein;
(ii) transfecting the mammalian cell obtained in (i) with the remaining any one or more of the first genetic entity, the second genetic entity, the third genetic entity, and the fourth genetic entity as defined herein; and
(iii) culturing the mammalian cell obtained in (ii) under conditions allowing for the expression of the nucleic acid sequence of interest.

In one embodiment, the method is performed as in vitro or ex vivo method.

In a specific embodiment, step (i) and/or step (ii) comprise(s) a stable transfection. In another specific embodiment, step (i) and/or step (ii) comprise(s) a transient transfection.

In another specific embodiment, the method further comprises the step of harvesting (and optionally purifying) the recombinant polypeptides or proteins produced. Depending on their nature the polypeptides or proteins may become secreted into the cell culture supernatant, integrated in membrane of the host cell, or remain in an intracellular compartment.

Typically, if a unicellular mammalian host cell is employed the person skilled in the art can revert to a variety of cell culture conditions which allow for the expression of the nucleic acid sequence of interest. Conveniently, the polypeptides or proteins produced are harvested (and optionally purified) from the culture medium, lysates or extracts of the cultured cells by established techniques, such as inter alia fractionated precipitation with salts or organic solvents, ion exchange chromatography, gel chromatography, size exclusion chromatography, HPLC, affinity chromatography (see, e.g., Sambrook, J., and Russel, D. W. (2001), supra). In case, the host cell is part of a multi-cellular organism, a fraction of these cells may serve as source for isolating the peptide of the invention.

Appropriate culture media and conditions for the above-described host cells are well known in the art (cf., e.g., Fresney, R. I. (2000) *Culture of Animal cells. A manual (4th Ed.)* Wiley-Liss, New York). Depending on the specific growth requirements of the host cell employed, mammalian cell culture can be performed, e.g., in RPMI 1640 medium, Ham's F12 medium or DMEM (Dulbecco's Modified Eagle Medium). Alternatively, a growth medium with a reduced serum concentration, such as OptiMEM, may be used. The media may optionally be supplemented with 10% (v/v) FCS (fetal calf serum), various growth factors, amino acids, antibiotics, and other additives Cell culture media specially adapted for CHO cells are described in, e.g., EP 0 481 791 B1 and EP 1 525 320 B1. The transfected mammalian host cells may be incubated at 37° C. in a 5% $CO_2$, water saturated atmosphere. The respective growth media, kits, and reagents are commercially available from various suppliers.

Finally, the present invention relates to the use of the expression system as defined herein as molecular tool for enhancing heterologous nucleic acid expression in mammalian cells.

The invention is further described by the figures and the following examples, which are solely for the purpose of illustrating specific embodiments of this invention, and are not to be construed as limiting the scope of the invention in any way.

EXAMPLES

Example 1

Materials and Methods 1.1 Vector Construction

For construction of the control vector utilized in transient experimentation, the eGFP gene was amplified via PCR using fwd-eGFP and rev-eGFP primers (shown in Table 1) and the peGFP-N1 vector (Clontech Laboratories Inc., Mountain View, Calif., USA) as a template. Subsequently, NheI and BglII restriction enzymes were used to insert the amplified fragment such that the eGFP is located downstream of an SV40 promoter allowing for efficient expression of the gene (FIG. 1A). The minimal OriP DNA-binding units were synthesized commercially (by Geneart) and sub-cloned into the eGFP vector using BamHI and SalI enzymes (FIG. 1B). The truncated EBNA-1 gene was amplified using the fwd-EBNA and rev-EBNA primers. XbaI and AgeI restriction enzymes were used to insert the gene upstream of the first hCMV-MIE promoter in the previously generated eGFP vector. In addition, the minimal OriP units (i.e., the 'Family of Repeats' DNA-binding site for EBNA-1 and the 'Dyad Symmetry' DNA-binding site for EBNA-1) were sub-cloned into this vector using the aforementioned method. (FIG. 1C). Similarly, fwd-NDPK-A and rev-NDPK-A primers were designed to amplify the NDPK-A gene (accession number XM_003501375) from a cDNA template derived from CHOK1SV. AscI and XhoI restriction enzymes were used to insert the NDPK-A gene downstream of the second hCMV-MIE promoter of the eGFP vector (FIG. 1D).

Figure 5:
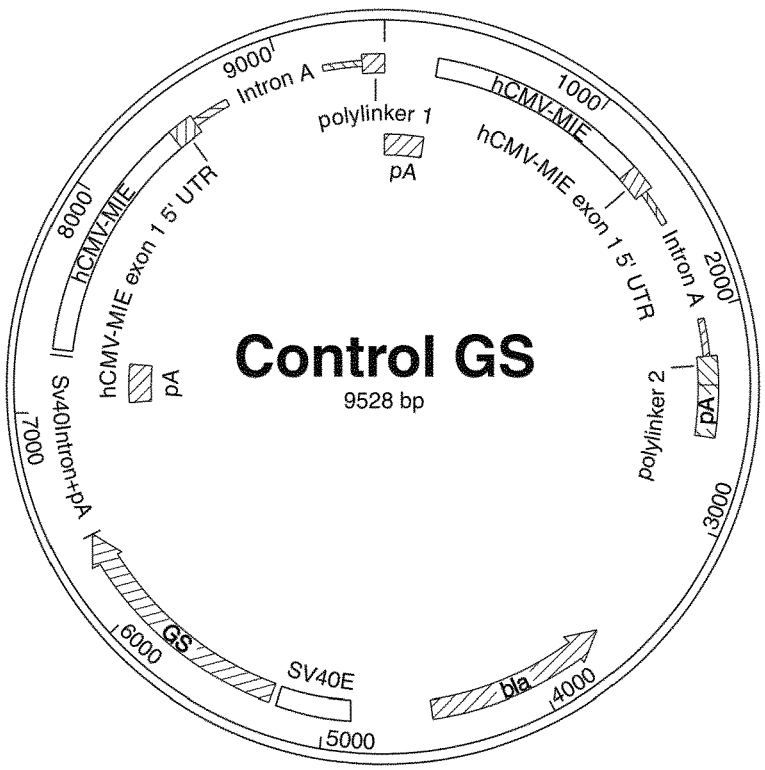
FIG. 5 schematically illustrates exemplary expression vectors generated for stable transfection studies. All vectors encompass the gene encoding glutamine synthase (GS) as selection marker. (A) Control vector. (B) Vector including a nucleic acid sequence encoding NDPK-A. (C) Vector including a nucleic acid sequence encoding EBNA-1. (D) Vector including nucleic acid sequences encoding NDPK-A and EBNA-1. Images prepared by using the SnapGene software.
Figure 5:
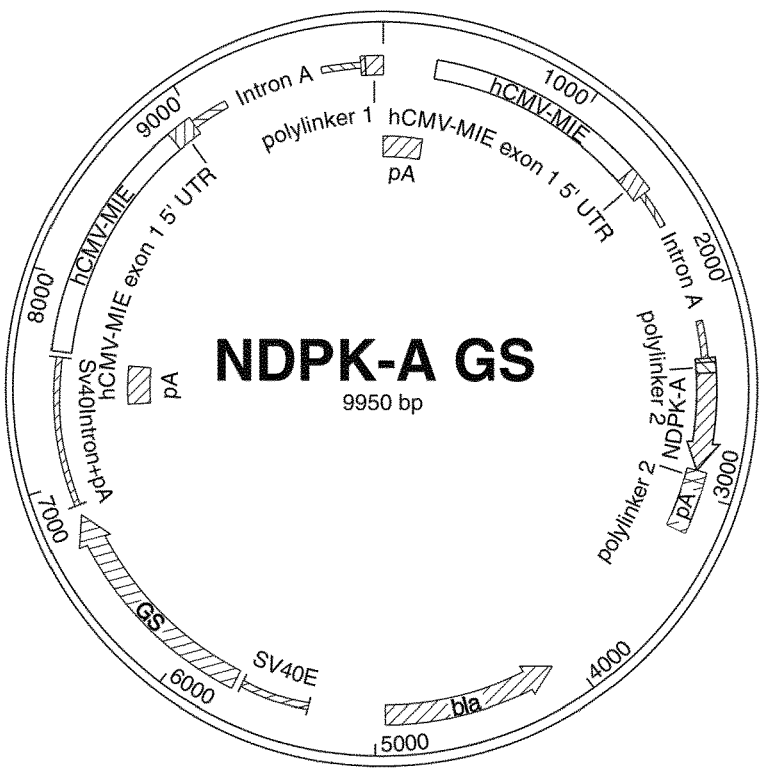
Figure 5:
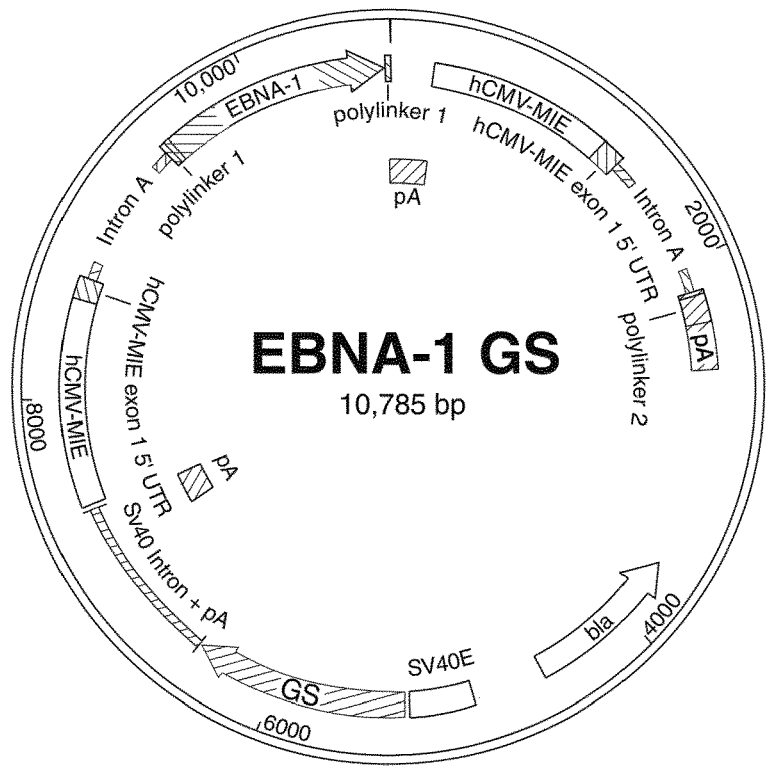
Figure 5:
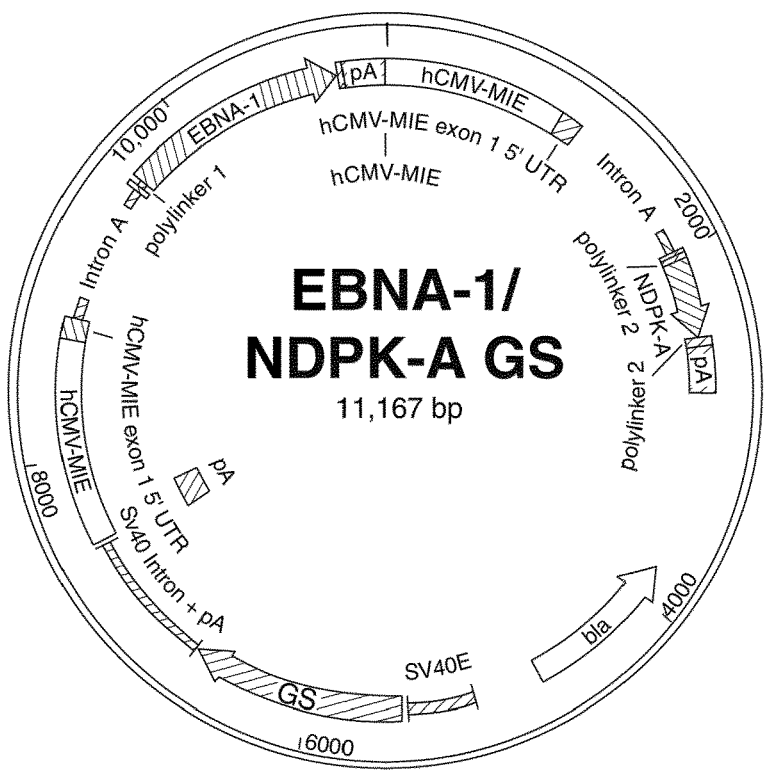

The glutamine synthetase gene was sub-cloned into eGFP and NDPK-A vectors as well as the EBNA-1 precursor plasmid downstream of the SV40 promoter using the NheI and BglII restriction enzymes to generate Control GS, NDPK-A GS and EBNA-1 GS constructs respectively (FIG. 5A-C). The NDPK-A gene was subsequently cloned downstream of the second hCMV-MIE promoter into the EBNA-1 GS plasmid such that the EBNA-1 truncated gene and NDPK-A gene are under the control of separate promoters (FIG. 5B).

TABLE 1

Oligonucleotide primers used herein

| SEQ ID NO: | Name | Primer Sequence (5' → 3') |
| --- | --- | --- |
| 10 | fwd-eGFP | TATGCTAGCGGTACCATGGTGAGCAAGGGCGAGGA |
| 11 | rev-eGFP | ATAAGATCTGGTACCCTTGTACAGCTCGTCCATGC |
| 12 | fwd-EBNA | TATTCTAGAATGTCTGACGAGGGGCCAGGTACAGG |
| 13 | rev-EBNA | ATAACCGGTTCACTCCTGCCCTTCCTCACCC |
| 14 | fwd-NDPK-A | TATGGCGCGCCATGGCCAACAT |
| 15 | rev-NDPK-A | ATACTCGAGTCACTCATAGATCCAGTTTTGTGCACAGCT |

1.2 Cell Culture

CHOK1SV, CHOK1SV GS (Xceed) (both of Lonza Ltd, Basel, Switzerland), and CHO 9B cells were maintained as suspension cultures in CD-CHO media (Gibco BRL/Life Technologies Inc., Carlsbad, Calif., USA) supplemented with 6 mM L-glutamine. Stable cell lines were routinely maintained using CD-CHO media supplemented with 25 µM MSX. Cells were passaged every 3-4 days as necessary and seeded at a density of $0.2 \times 10^6$ viable cells/ml into 125 ml Erlenmyer flasks. These cultures were incubated at 37° C. at 140 rpm and cultured under a 5% $CO_2$ gas environment.

1.3 Transient Transfections

CHO suspension cells were transfected by means of electroporation. Cells were centrifuged at 1000 rpm for 10 minutes, the supernatant was removed, and the pellet suspended at a density of $14.3 \times 10^6$ cells/m in fresh pre-warmed medium and placed in a water-bath at 37° C. A Genepulser Xcell electroporator (Bio-Rad Laboratories GmbH, Munich, Germany) was used to perform the electroporation. A Bio-Rad cuvette (diameter 0.4 mm) was used to produce a 20 ml culture. 20 µg DNA, in 100 µl TE buffer, and 700 µl cell suspension ($10 \times 10^6$ cells) were added to the cuvette. The DNA/cell mix was treated at 300 V and 900 µF. 1 ml of pre-warmed medium was added to the cuvette immediately after electroporation. The transfected cells were then added to a flask containing the appropriate volume for the number of cuvettes used (minus the volume of the cells and the media for the wash). 1 ml of medium was used to wash the cuvette and added to the flask. 5% $CO_2$ balance air was added to the flask based on the culture volume (as performed with routine subculture) and incubated in a shaking incubator at 140 rpm at 37° C.

1.4 Generation of Stable Cell Lines

The glutamine synthetase (GS) containing expression vectors (FIG. 5) were cleaved using PvuI restriction enzyme. The linearized DNA was purified by ethanol precipitation and transfected into CHOK1SV GS cells as described above. Transfected cells were cultured in a T75 flask in CD-CHO media at 37° C. in a static incubator maintaining a 5% $CO_2$ environment. 24 hours post transfection, L-methionine sulfoximine (MSX) was added for selection at a final concentration of 25 µM. The MSX supplemented medium was renewed approximately every five days until cells reached a viable cell count of above $0.2 \times 10^6$ cells/ml. Cells were transferred to a 125 ml Erlenmeyer flask and maintained as outlined above.

1.5 Flow Cytometry

Cell samples were centrifuged at 1000 rpm for 5 minutes and suspended in 500 µl phosphate buffered saline (PBS). Samples were then loaded onto the probe of a FACScalibur (BD Biosciences, Heidelberg, Germany) and fluorescence intensity was measured in relation to the cell count. The forward scatter (FSC) was measured using the E-1 amplifier and side scatter (SSC) set to 465 whilst FL1 recorded cells at 473; all settings were converted to Log scales. Data obtained via flow cytometry and presented in figures in the results section show either the percentage cells exceeding a $10^1$, $10^2$ or $10^3$ fluorescence threshold, termed M1, M2 and M3 respectively, or the mean fluorescence including all recorded cells of a sample.

1.6 Western Blot Analysis

SDS-PAGE was used to resolve polypeptides from protein lysates. 10 µg total protein lysate was loaded per lane and separated using a 12% polyacrylamide gel. For analysis of monoclonal antibody amounts in cell culture supernatants, an equal volume of cell culture supernatant from each sample was analyzed in each lane. Subsequently, polypeptides were transferred to a nitrocellulose membrane and blocked for 30 minutes in a 5% w/v powdered milk solution in 0.2% Tween TBS. Primary anti-GFP mouse monoclonal GFP 3E1 antibody (obtained from Research Monoclonal Antibody Service, CR-UK; dilution 1:5000) and anti-β-actin mouse monoclonal was exposed to membrane overnight and anti-mouse IgG (whole molecule) peroxidase conjugated secondary antibody produced in goat (Sigma-Aldrich, Munich, Germany) was used for chemiluminescent detection of relevant polypeptides using Hyperfilm ECL reagents (GE Healthcare GmbH, Munich, Germany). An anti-heavy chain antibody from Sigma-Aldrich (Munich, Germany) was used for western analysis of secreted, intact monoclonal antibodies found in cell culture supernatants. Quantitative densitometry was analyzed using ImageJ software.

Example 2

Effect of NDPK-A Gene Expression on Transfection Efficacy in CHO Cells

In order to evaluate the effect of NDPK-A (NME1) on transient gene expression, respective expression vectors encompassing the NDPK-A nucleic acid sequence were transiently transfected into CHOK1SV, CHOK1SV GS, and CHO9B (data not shown) suspension cell lines by means of electroporation, respectively. The enhanced green fluorescent gene was used as selection marker. Analysis was subsequently undertaken using flow cytometry to identify both the percentage of cells expressing eGFP and the amount expressing eGFP beyond a pre-determined threshold. Representative experimental results are shown in FIG. 2, FIG. 4, FIG. 6, and FIG. 7, respectively.

In all three CHO cell lines analyzed (some data not shown), the percentage of cells that exceed a fluorescence intensity threshold upon transient transfection was substantially enhanced with concomitant expression of the NDPK-A nucleic acid sequence, which suggests an increased rate of nuclear uptake in these cells.

Example 3

EBNA-1 and OriP Induced Extrachromosomal Maintenance in CHO Cells

The effect of EBNA-1 and OriP elements (i.e., the 'Family of Repeats' DNA-binding site for EBNA-1 and the 'Dyad Symmetry' DNA-binding site for EBNA-1) on transient transfection, and in particular on the induction of extrachromosomal maintenance of the transfected expression vectors, was analyzed in CHOK1SV, CHOK1SV GS, and CHO9B suspension cell lines, respectively. A vector encoding the eGFP gene was used as a negative control and vectors encoding an EBNA-1 nucleic acid sequence and a combination of EBNA-1 and the OriP sequences, respectively, were transiently transfected via electroporation. The percentage of cells that exceeded a fluorescence intensity threshold were measured by means of flow cytometry at various time points post transfection as an indication of induced extrachromosomal maintenance. Representative experimental results are shown in FIG. 3, FIG. 4, FIG. 6, FIG. 7, and FIG. 8, respectively.

In all three CHO cell lines analyzed (some data not shown), the percentage of cells that exceed a fluorescence intensity threshold upon transient transfection was substantially enhanced with concomitant expression of the EBNA-1 nucleic acid sequence. The additional presence of the OriP sequences resulted in a further substantial increase in transient transfection efficiency, caused by improved extrachromosomal maintenance. The most pronounced effect could be observed in CHOK1SV GS ("Xceed") cells.

Example 4

Figure 4:
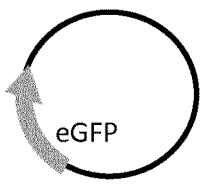
FIG. 4 illustrates the combined effect of using NDPK-A and EBNA-1 in order to enhance transfection efficacy in CHO cells. (A) Schematic representation of the three expression vectors employed and the combinations used for transfecting the CHO cells. Twice the amount of vector DNA has been used in the control/control sample to ensure that the same amount of DNA has been used in all samples. Shown is the percentage of CHO cells expressing the eGFP gene at various time points 24 to 168 hours post-transfection with the respective combinations of expression vectors using different fluorescence intensity thresholds: (B) $10^1$, (C) $10^2$, and (D) $10^3$. Data represent means±SEM of three independent experiments. The results demonstrate that simultaneous co-transfection with the NDPK-A and EBNA-1 encoding expression vectors results in a higher percentage of cells expressing eGFP for a longer period of time (as compared to the control construct) than transfections using either construct independently. The increase in mean fluorescence is shown in (E).
Figure 4:
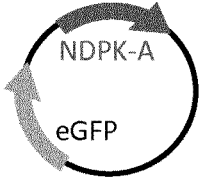
Figure 4:
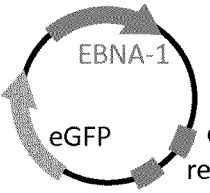
Figure 4:
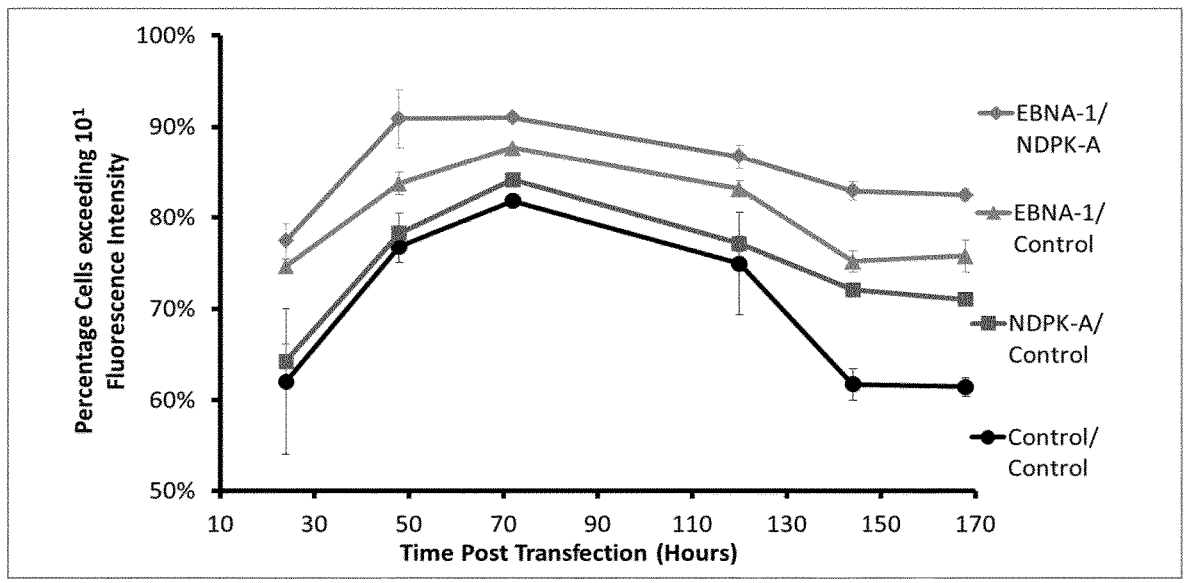
Figure 4:
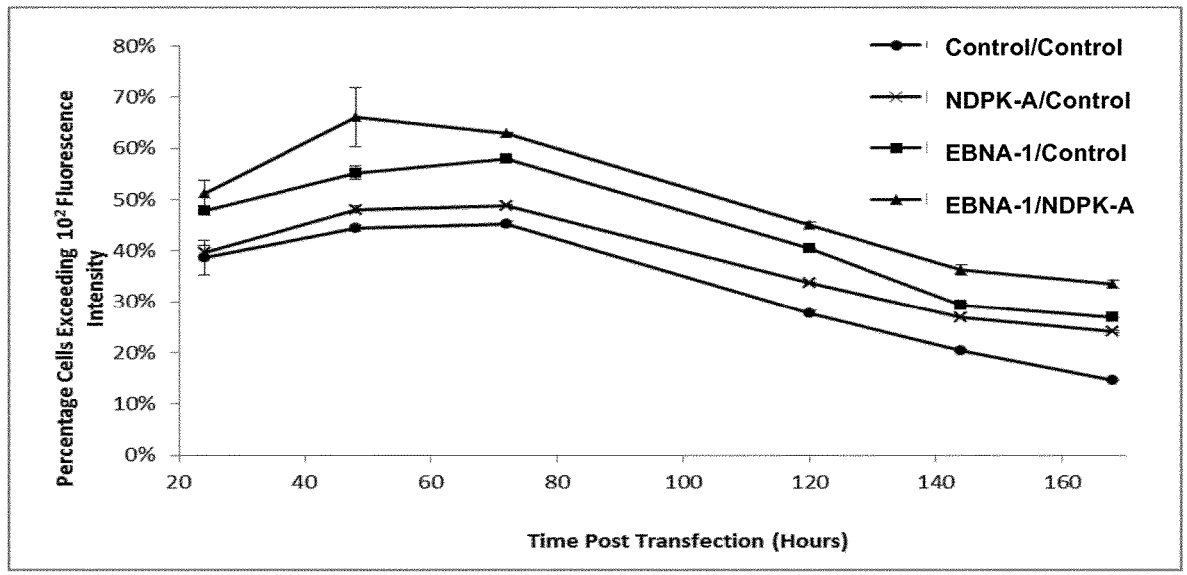
Figure 4:
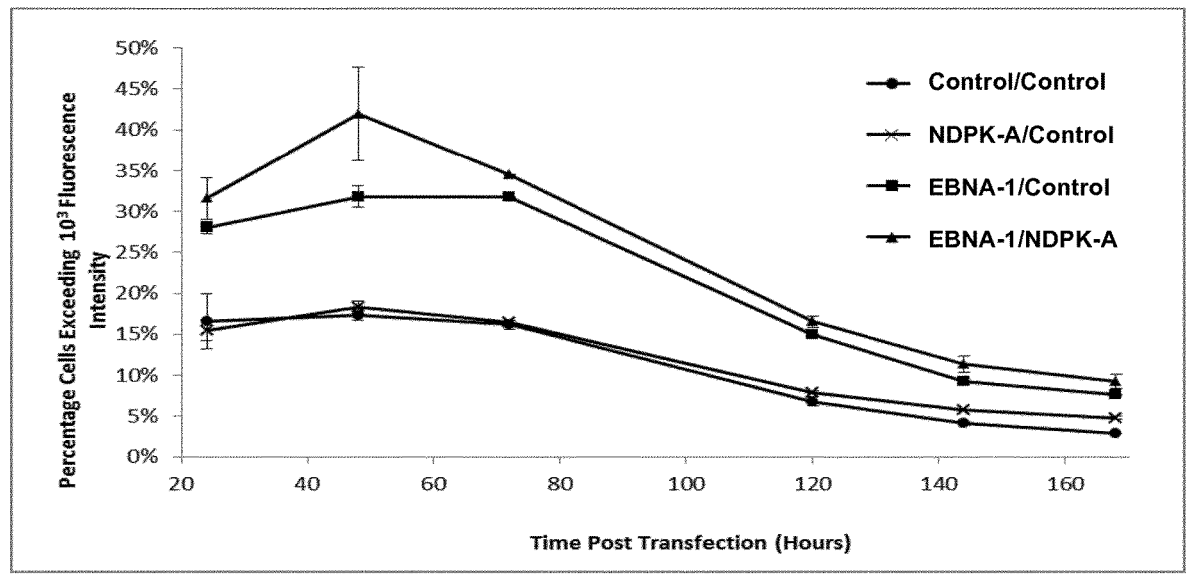
Figure 4:
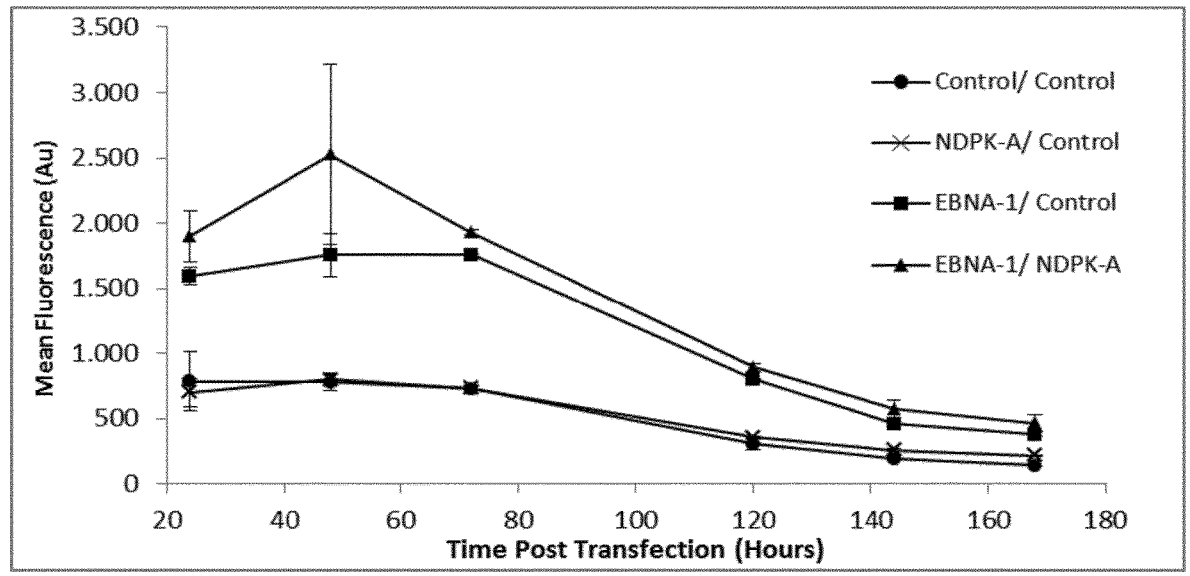
Figure 6:
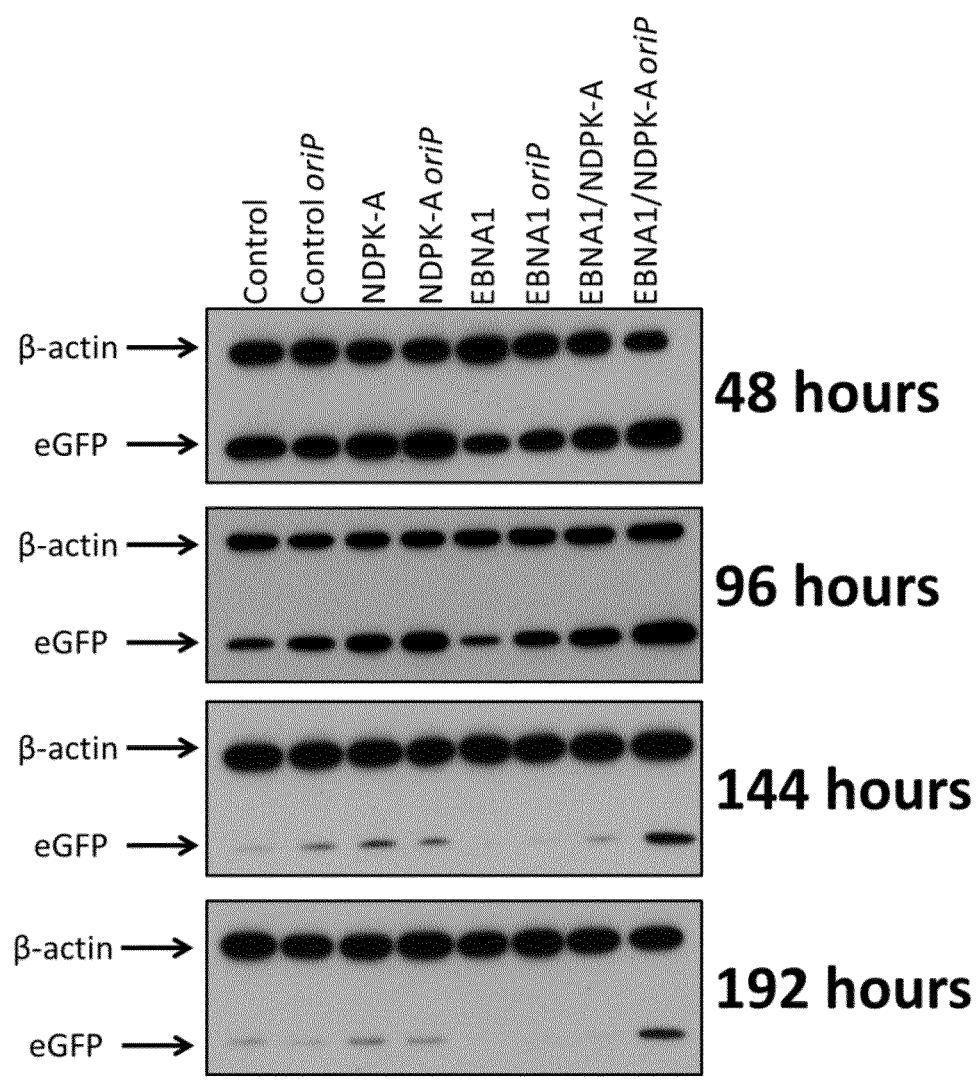
FIG. 6 illustrates the results of a representative Western blot analysis showing the amounts of eGFP produced in CHOK1SV GS cells ("CHO Xceed", Lonza Ltd., Basel, Switzerland) at various time points after transient transfection with the respective expression vectors depicted in FIG. 1 and FIG. 5, including or lacking the OriP sequences in stable cell lines expressing NDPK-A, EBNA-1, and NDPK-A/EBNA-1, respectively. β-actin levels are used as control.
Figure 7:
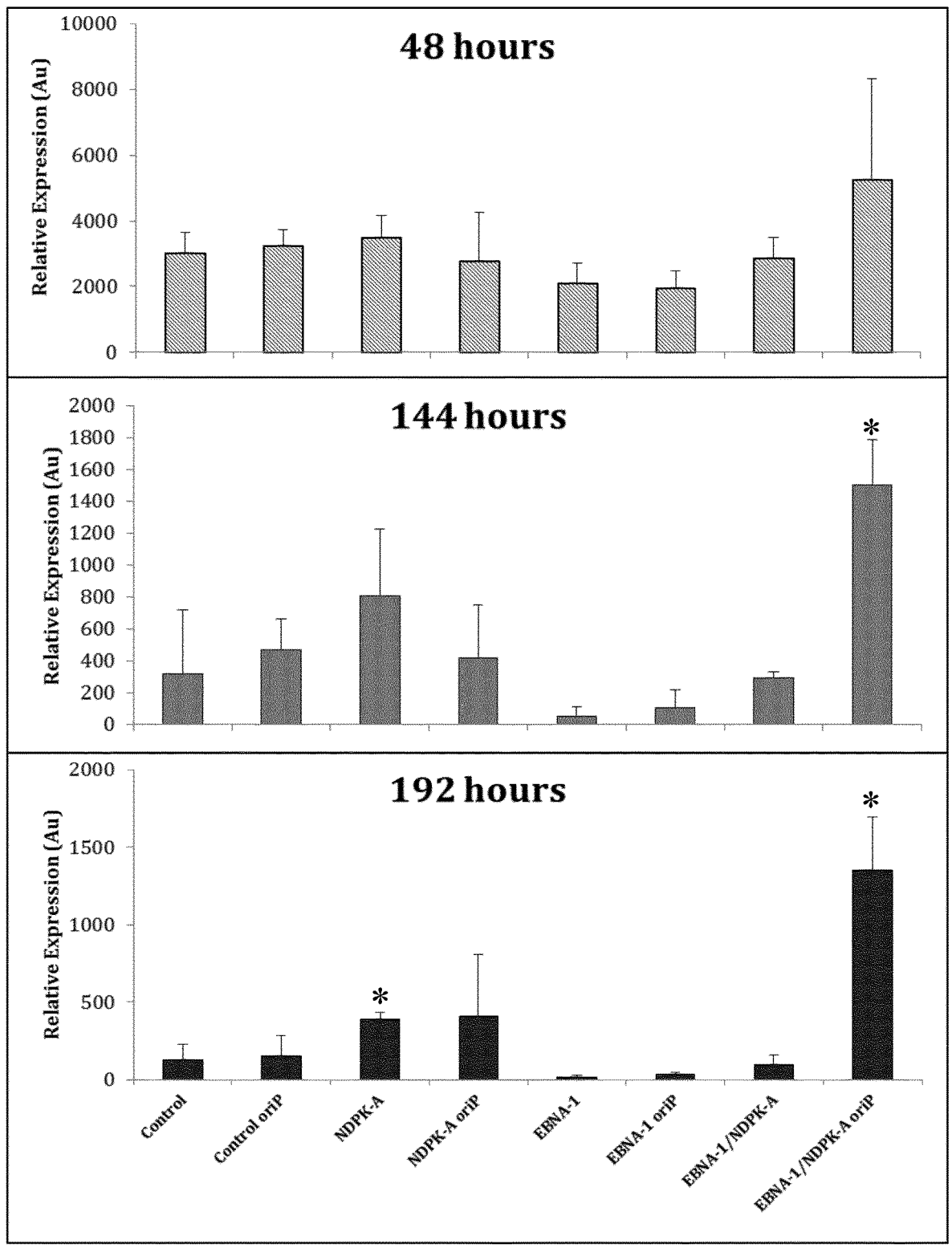
FIG. 7 illustrates the results of a quantitative densitometry analysis of eGFP protein expression (as compared to a control cell line) of the same transfected cells shown in FIG. 6. The data confirm a further improvement in the presence of the OriP sequences. * $p<0.05$.
Figure 8:
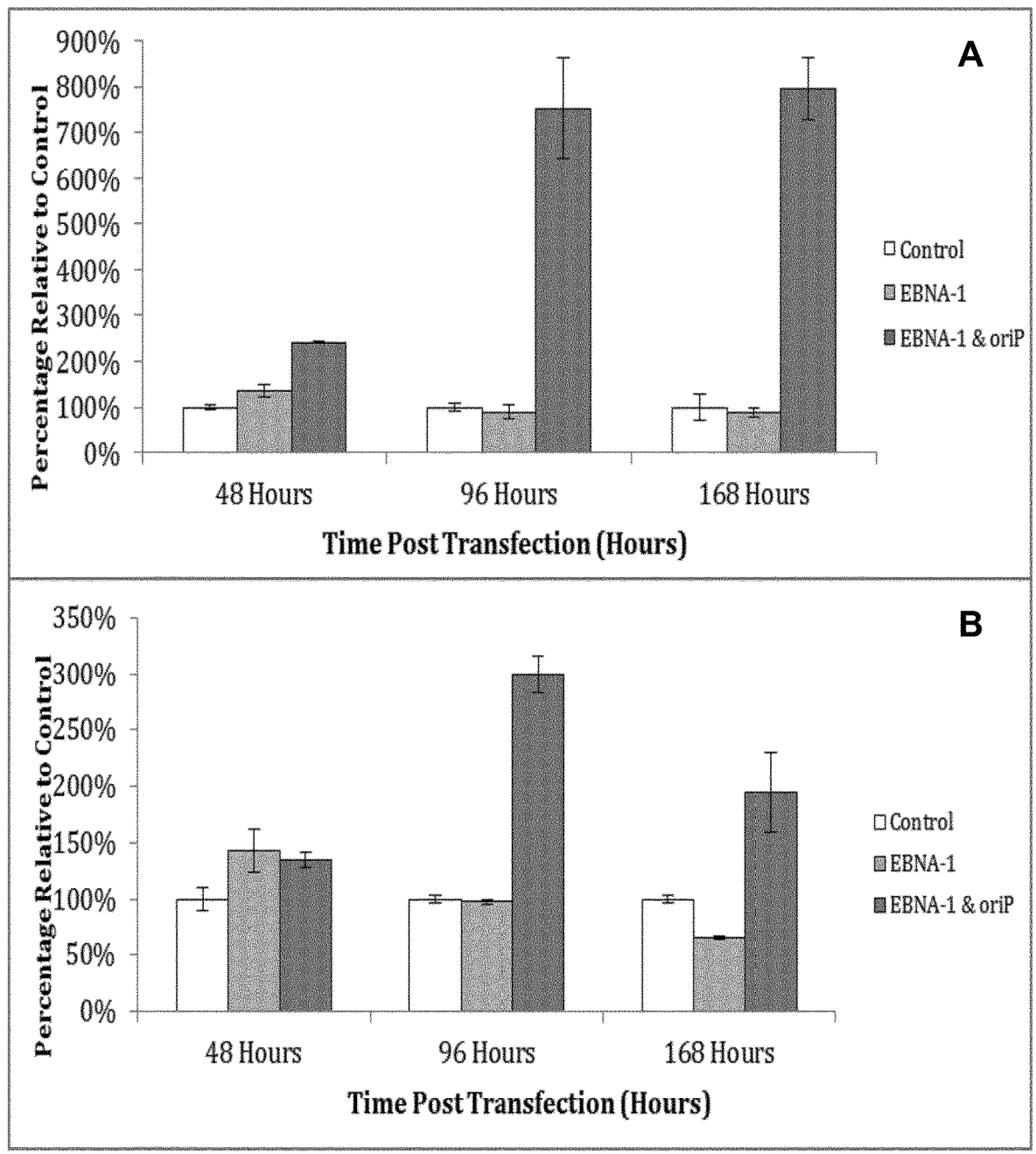
FIG. 8 illustrates the effect of EBNA-1 in order to enhance transfection efficacy. Depicted are the results of representative transient transfection experiments using CHOK1SV GS cells (A) and CHO 9B cells (B), respectively and control, EBNA-1, and EBNA-1/OriP expression vectors shown in FIG. 5. Data are expressed as percentage of eGFP gene expression relative to control levels after 48, 96, and 168 hours post transfection and are given as mean±SEM of three experiments. The data demonstrate a significant improvement in the presence of the OriP sequences.

Combined Effect of EBNA-1 and NDPK-A Gene Expression on Transient Transfection Efficacy in CHO Cells The combined effect of NDPK-A and EBNA-1 gene expression (in the presence or absence of OriP elements (i.e., the 'Family of Repeats' DNA-binding site for EBNA-1 and the 'Dyad Symmetry' DNA-binding site for EBNA-1)) on transient transfection was analyzed in CHOK1SV, CHOK1SV GS, and CHO9B suspension cell lines, respectively. A vector encoding the eGFP gene was used as a negative control. The respective expression vectors (encoding NDPK-A, NDPK-A+OriP, EBNA-1, EBNA-1+OriP, NDPK-A+EBNA-1, NDPK-A+EBNA-1+OriP) were transiently transfected via electroporation. The percentage of cells that exceeded a fluorescence intensity threshold were measured by means of flow cytometry at various time points post transfection as an indication of induced extrachromosomal maintenance. Representative experimental results are shown in FIG. 4, FIG. 6, and FIG. 7, respectively.

Example 5

Figure 9:
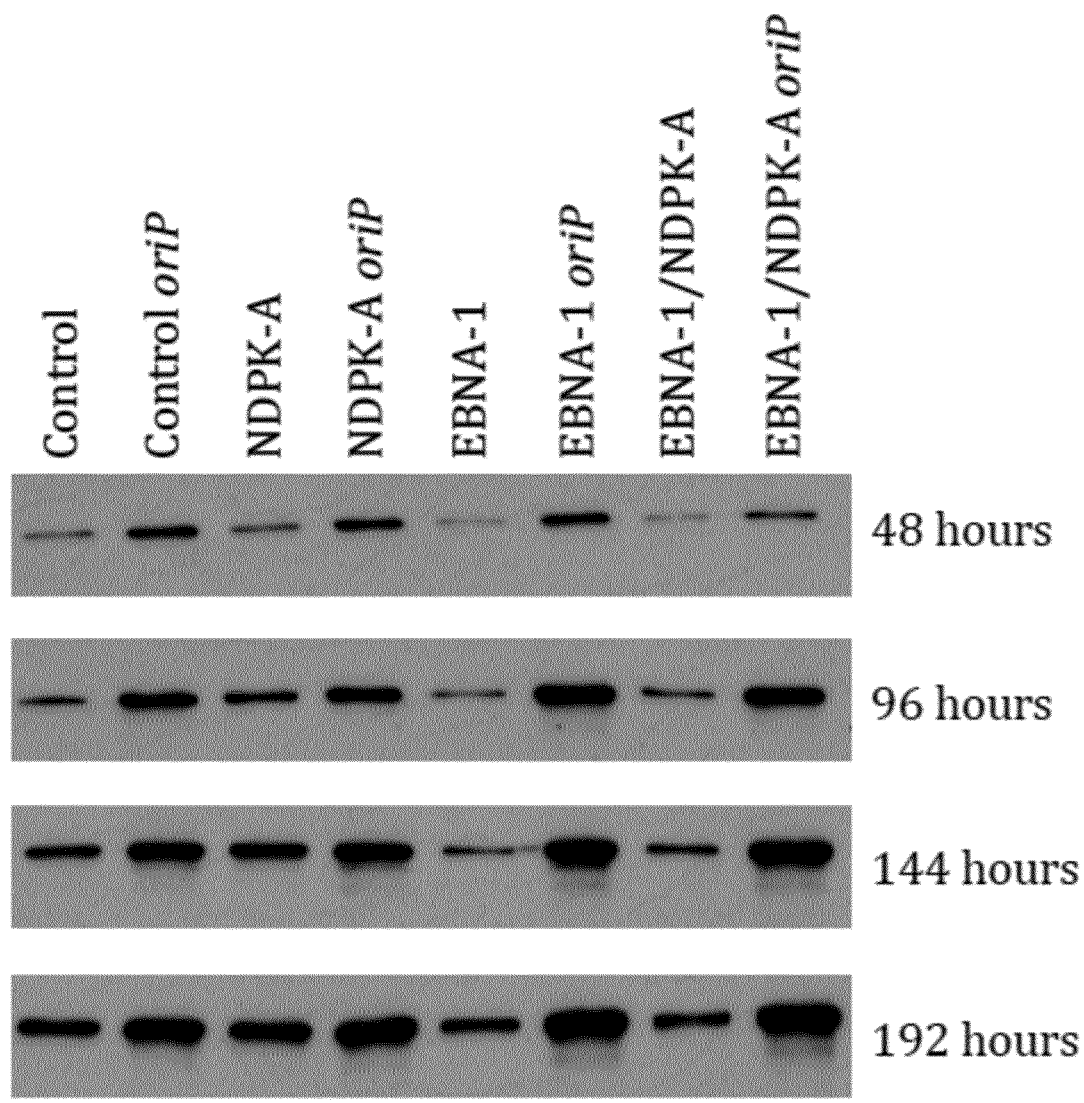
FIG. 9 illustrates the results of a representative Western blot analysis showing the amounts of a model IgG4 monoclonal antibody, cB72.3, secreted into the cell culture supernatant produced at various time points (48, 96, 144 or 196 hours post-transfection) upon transient transfection with expression vectors including or lacking the OriP sequences in stable cell pools expressing NDPK-A, EBNA-1, and NDPK-A/EBNA-1, respectively.

Combined Effect of Stable EBNA-1 and NDPK-A Gene Expression With or Without OriP Elements on Transient Monoclonal Antibody Expression in CHO Cells The combined effect of NDPK-A and EBNA-1 gene expression (in the presence or absence of OriP elements (i.e., the 'Family of Repeats' DNA-binding site for EBNA-1 and the 'Dyad Symmetry' DNA-binding site for EBNA-1)) on transient transfection and expression of a model monoclonal antibody (cB72.3) was analyzed in stably generated NDPK-A, EBNA-1 or EBNA-1/NDPK-A cell pools. These stably expressing cell pools were transiently transfected with a plasmid containing the heavy and light chains of the cB72.3 monoclonal IgG4 antibody, and the amount of intact antibody in the cell culture supernatant at various time points post-transfection was analyzed via Western blot. Representative experimental results are shown in FIG. 9, demonstrating that the EBNA-1/NDPK-A cell pool containing the OriP elements consistently revealed the presence of the highest amount of antibody at all time points investigated post-transfection.

The data obtained showed that, in all cell lines tested (some data not shown), the co-expression of the NDPK-A and EBNA-1 nucleic acid sequences resulted in an additive or even synergistic improvement of transfection efficacy as compared to the individual expression of either nucleic acid sequence. The additional presence of the OriP sequences caused a further improvement of transfection efficacy.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A mammalian cell for the heterologous expression of a nucleic acid sequence of interest, the mammalian cell comprising:
   (i) a first genetic entity, comprising: a nucleic acid sequence encoding a functional Epstein Barr virus nuclear antigen 1 (EBNA-1), the nucleic acid sequence being operably linked to regulatory elements that allow for expression of the nucleic acid sequence encoding a functional EBNA-1;
   (ii) a second genetic entity, comprising: a nucleic acid sequence encoding a functional nucleoside diphosphate kinase A (NDPK-A) comprising a nuclear localization sequence (NLS), the nucleic acid sequence being operably linked to regulatory elements that allow for expression of the nucleic acid sequence encoding a functional NDPK-A;
   (iii) a third genetic entity, comprising: the nucleic acid sequence of interest being operably linked to regulatory elements that allow for expression of the nucleic acid sequence of interest; and
   (iv) a fourth genetic entity, comprising an Epstein Barr virus origin of replication P (OriP) sequence comprising at least the 'Family of Repeats' DNA-binding site for EBNA-1 and the 'Dyad Symmetry' DNA-binding site for EBNA-1
   wherein the mammalian cell is a CHO cell.

2. The mammalian cell of claim 1, wherein any one or more of the first genetic entity, the second genetic entity, the third genetic entity, and the fourth genetic entity are capable of independent replication.

3. The mammalian cell of claim 1, wherein any one or more of the first genetic entity, the second genetic entity, the third genetic entity, and the fourth genetic entity are comprised in one or more vectors, wherein:
   (a) any one of the first genetic entity, the second genetic entity, the third genetic entity, and the fourth genetic entity is comprised in a vector;
   (b) any two of the first genetic entity, the second genetic entity, the third genetic entity, and the fourth genetic entity are comprised in the same vector;
   (c) any three of the first genetic entity, the second genetic entity, the third genetic entity, and the fourth genetic entity are comprised in the same vector; or
   (d0 all four of the first genetic entity, the second genetic entity, the third genetic entity, and the fourth genetic entity are comprised in the same vector.

4. The mammalian cell of claim 3, wherein (a) the first genetic entity and the second genetic entity are comprised in a first vector; and (b) the third genetic entity and the fourth genetic entity are comprised in a second vector.

5. The mammalian cell of claim 1, the mammalian cell being further characterized by any one or more of the following structural features:
   (a) the nucleic acid sequence encoding a functional EBNA-1 is selected from the group of sequences consisting of SEQ ID NO: 1 and SEQ ID NO: 2;
   (b) the nucleic acid sequence encoding a functional NDPK-A has the sequence of SEQ ID NO: 3;
   (c) the nucleic acid sequence encoding the 'Family of Repeats' DNA-binding site for EBNA-1 has the sequence of SEQ ID NO: 4 and the nucleic acid sequence encoding the 'Dyad Symmetry' DNA-binding site for EBNA-1 has the sequence of SEQ ID NO: 5; and
   (d) the mammalian cell further comprises at least one nucleic acid sequence encoding a selection marker.

6. The mammalian cell of claim 1, wherein the nucleic acid sequence of interest encodes an antibody or an antibody fragment.

7. A method for the expression of a nucleic acid sequence of interest in a mammalian cell, comprising:
   (i) transfecting a mammalian cell with any one or more of the first genetic entity, the second genetic entity, the third genetic entity, and the fourth genetic entity as defined in claim 1;
   (ii) transfecting the mammalian cell obtained in (i) with the remaining any one or more of the first genetic entity, the second genetic entity, the third genetic entity, and the fourth genetic entity as defined in claim 1; and
   (iii) culturing the mammalian cell obtained in (ii) under conditions allowing for the expression of the nucleic acid sequence of interest.

8. The method of claim 7, wherein step (i) and/or step (ii) comprises a stable transfection.

9. The method of claim 7, wherein step (i) and/or step (ii) comprises a transient transfection.

10. The mammalian cell of claim 4, wherein the first vector does not comprise a functional Epstein Barr virus OriP sequence, and the second vector does not comprise a nucleic acid sequence encoding a functional EBNA-1.

11. The mammalian cell of claim 5, wherein the selection marker defined in (d) is glutamine synthase.

12. The mammalian cell of claim 1, wherein the CHO cell lacks glutamine synthase.

* * * * *